United States Patent [19]

Kumazawa

[11] Patent Number: 5,885,771
[45] Date of Patent: Mar. 23, 1999

[54] ANTIGENIC PEPTIDE COMPOUND AND IMMUNOASSAY

[75] Inventor: Toshiaki Kumazawa, Tokyo, Japan

[73] Assignee: SRL, Inc., Tokyo, Japan

[21] Appl. No.: 617,929

[22] PCT Filed: Oct. 28, 1994

[86] PCT No.: PCT/JP94/01823
  § 371 Date: Apr. 24, 1996
  § 102(e) Date: Apr. 24, 1996

[87] PCT Pub. No.: WO95/11918
  PCT Pub. Date: May 4, 1995

[30] Foreign Application Priority Data

Oct. 29, 1993 [JP] Japan .................................. 5-272864
Aug. 31, 1994 [JP] Japan .................................. 6-207695

[51] Int. Cl.$^6$ .......................... C12Q 1/70; G01N 33/569; A61K 39/29; A61K 39/295
[52] U.S. Cl. .............................. 435/5; 435/7.1; 435/69.3; 530/300; 530/324; 530/326; 530/806; 530/826
[58] Field of Search ............................... 435/5, 7.1, 69.3; 530/300, 350, 326, 324, 806, 826

[56] References Cited

FOREIGN PATENT DOCUMENTS

| | | |
|---|---|---|
| 463848 | 1/1992 | European Pat. Off. . |
| 464287 | 1/1992 | European Pat. Off. . |
| 468657 | 1/1992 | European Pat. Off. . |
| 532167 | 3/1993 | European Pat. Off. . |
| 5-176773 | of 1993 | Japan . |
| 2239245 | 6/1991 | United Kingdom . |
| WO 89 04669 | 6/1989 | WIPO . |
| 9219743 | of 1993 | WIPO . |
| 9300365 | of 1993 | WIPO . |
| 9310239 | of 1993 | WIPO . |
| 9310854 | 9/1993 | WIPO . |
| 9317110 | 9/1993 | WIPO . |

OTHER PUBLICATIONS

Choo et al, "Isolation of a cDNA Clone Derived from a Blood–Borne Non–A, Non–B Viral Hepatitis Genome", Science, Apr. 1989, vol. 244, pp. 359–363.
Kuo et al, "An Assay for Circulating Antibodies to a Major Etiologic Virus of Human Non–A, Non–B Hepatitis", Science, Apr. 1989, vol. 244, pp. 362–364.
Bradley et al, "Posttransfusion Non–A, Non–B Hepatitis in Chimpanzees", Gastroenterology, vol. 88, 1985, pp. 773–779.
Takamizawa et al, "Structure and Organization of the Hepatitis C Virus Genome Isolated from Human Carriers", Journal of Virology, 1991, vol. 65, No. 3, pp. 1105–1113.
Klyosawa et al, "The Clinical Usefulness of a New (the Second Generation) Antibody to Hepatitis C Virus", Japan Journal of Clinical Pathology 40, pp. 1245–1251, 1992.
Okamoto, KAN TAN SUI, vol. 24, pp. 7–14, 1992.
Choo et al, "Genetic organization and diversity of the hepatitis C virus", Proc. Natl. Acad. Sci. USA, vol. 88, pp. 2451–2455, Biochemistry, 1991.
Okamoto, "Nucleotide sequences of the genomic RNA of hepatitis C virus isolated from a human carrier: comparison with reported isolates for conserved and divergent regions", J. of Gen. Virol., 1991, vol. 72, pp. 2697–2704.
Okamoto et al, "Full–Length Sequence of a Hepatitis C Virus Genome Having Poor Homology to Reported Isolates: Comparative Study of Four Distinct Genotypes", Virology 188, pp. 331–341, 1992.
Proceedings of the 29th Meeting of Acta Hepatologica, Japanica, p. 55, 1993.
Kan Tan Sui, vol. 22, pp. 883–889, 1991.
Smith et al, "Infectious vaccinia virus recombinants that express hepatitis B virus surface antigen", Nature, vol. 302, No. 7, Apr. 1983.
Hopp et al, "Prediction of protein antigenic determinants from amino acid sequences", Proc. Natl. Acad. Sci. USA, vol. 78, 1981, pp. 3824–3827.
Kyte et al, "A Simple Method for Displaying the Hydropathic Character of a Protein", J. Mol. Biol., vol. 157, pp. 105–132.
Moriarty et al, Antibodies to Peptides Detect New Hepatitis B Antigen: Serological Correlation with Hepatocellular Carcinoma, Science, vol. 227, 1985, pp. 429–433.
Sakakibara et al, "Use of Anhydrous Hydrogen Fluoride in Peptide Synthesis. I. Behavior of Various Protective Groups in Anhydrous Hydrogen Fluoride", Bulletin of the Chemical Society of Japan, vol. 40, No. 9, 1967, pp. 2164–2167.
Machida et al, "Two Distinct Subtypes of Hepatitis C Virus Defined by Antibodies Directed to the Putative Core Protein", Hepatology, vol. 16, No. 4, 1992, pp. 886–891.
Simmonds et al. 1993 J Clin Microbiol. 30:6, Jun. 30, 1993.

*Primary Examiner*—Marian C. Knode
*Assistant Examiner*—Mary K Zeman
*Attorney, Agent, or Firm*—Foley & Lardner

[57] ABSTRACT

An HCV antibody contained in a specimen is measured by an immunoassay method by utilizing the specific binding affinity of a hepatitis C virus (HCV) antibody to an antigenic peptide having the amino acid sequence represented by the following formula (1) or (2):

Leu-Ser-Gly-Arg-Pro-Ala-Ile-Val-Pro-Asp-Arg-Glu-Val-Leu-Tyr-Gln-Glu-Phe-Asp-Glu . . . (SEQ ID NO: 1)
  Val-Asn-Gln-Arg-Ala-Val-Val-Ala-Pro-Asp-Lys-Glu-Val-Leu-Tyr-Glu-Ala-Phe-Asp-Glu . . . (SEQ ID NO: 2)

According to the above method, it is possible to determine the serotype of the specimen simply and accurately, while suppressing a cross reaction or a non-specific reaction. As a result, it is also possible to preliminarily predict the effect of interferon treatment in an accurate manner, and to simply observe the course of the curing or treatment for hepatitis C.

16 Claims, 33 Drawing Sheets

807-IT PARAM FILE#0  RUN#839  CHROMATOGRAM REPLOT
CHART SPEED 5mm/min
START DELAY 0.00min  ATTENUATION 512mV F.S.

% CALCULATION RESULT
WINDOW=0%  SCALE FACTOR=1.0000  PEAK AREA

| PEAK# | RT(min) | AREA | HEIGHT | MK | AREA% |
|---|---|---|---|---|---|
| 1 | 0.542 | 10328 | 1283 | V | 0.1844 |
| 2 | 0.833 | 3460 | 331 | V | 6.1773E-02 |
| 3 | 3.200 | 1535 | 171 |  | 2.7393E-02 |
| 4 | 6.100 | 1905 | 183 |  | 3.3998E-02 |
| 5 | 8.325 | 4536 | 420 |  | 8.1872E-02 |
| 6 | 10.192 | 92249 | 9103 | L | 1.6468 |
| 7 | 10.458 | 24785 | 5433 | L | 0.4424 |
| 8 | 10.733 | 5453539 | 453558 | LLL | 97.3544 |
| 9 | 12.517 | 1563 | 189 |  | 2.7902E-02 |
| 10 | 15.517 | 2838 | 212 |  | 5.0663E-02 |
| 11 | 16.517 | 3364 | 240 |  | 6.0044E-02 |
| 12 | 19.917 | 1587 | 164 |  | 2.8326E-02 |
|  | TOTAL | 5601737 | 471289 |  | 100.0000 |

807-IT PARAM FILE#0  RUN#827  CHROMATOGRAM REPLOT
CHART SPEED 5mm/min
START DELAY 0.00min  ATTENUATION 128mV F.S.

% CALCULATION RESULT
WINDOW=0%  SCALE FACTOR=1.0000  PEAK AREA

| PEAK# | RT(min) | AREA | HEIGHT | MK | AREA% |
|---|---|---|---|---|---|
| 1 | 2.542 | 1406 | 179 |  | 0.1345 |
| 2 | 3.425 | 2348 | 193 | V | 0.2247 |
| 3 | 3.742 | 2108 | 285 | V | 0.2017 |
| 4 | 4.233 | 2594 | 192 | V | 0.2482 |
| 5 | 5.825 | 2726 | 192 |  | 0.2608 |
| 6 | 8.908 | 2968 | 174 | L | 0.2840 |
| 7 | 9.450 | 6296 | 645 | L | 0.6024 |
| 8 | 9.992 | 1018162 | 76549 | LLL | 97.4261 |
| 9 | 11.508 | 2183 | 233 |  | 0.2089 |
| 10 | 18.767 | 4271 | 361 |  | 0.4086 |
| | TOTAL | 1045060 | 79004 | | 100.0000 |

807-IT PARAM FILE#0  RUN#946  CHROMATOGRAM REPLOT
CHART SPEED 5mm/min
START DELAY 0.00min   ATTENUATION 128mV F.S.

CALCULATION RESULT
WINDOW=0%  SCALE FACTOR=1.0000  PEAK AREA

| PEAK# | RT(min) | AREA | HEIGHT | MK | AREA% |
|---|---|---|---|---|---|
| 1 | 2.883 | 1114 | 167 |  | 0.1490 |
| 2 | 3.758 | 1178 | 161 |  | 0.1575 |
| 3 | 4.108 | 2907 | 443 |  | 0.3888 |
| 4 | 6.750 | 1543 | 182 | L | 0.2064 |
| 5 | 7.267 | 19684 | 1792 | L | 2.6327 |
| 6 | 7.800 | 719575 | 60311 | LLL | 96.2405 |
| 7 | 9.300 | 168 | 181 |  | 0.2251 |
|  | TOTAL | 747684 | 63238 |  | 100.0000 |

807-IT PARAM FILE#0   RUN#959   CHROMATOGRAM REPLOT
CHART SPEED 5mm/min
START DELAY 0.00min   ATTENUATION 128mV F.S.

%CALCULATION RESULT
WINDOW=0%  SCALE FACTOR=1.0000   PEAK AREA

| PEAK# | RT(min) | AREA | HEIGHT | MK | AREA% |
|---|---|---|---|---|---|
| 1 | 4.083 | 10673 | 1497 | | 1.0765 |
| 2 | 7.750 | 980743 | 82731 | | 98.9235 |
| | TOTAL | 991416 | 84228 | | 100.0000 |

START DELAY 0.00min  CHART SPEED 5mm/min
ATTENUATION 128mV F.S.

%CALCULATION RESULT
WINDOW=0%  SCALE FACTOR=1.0000  PEAK AREA

| PEAK# | RT(min) | AREA | HEIGHT | MK | AREA% |
|---|---|---|---|---|---|
| 1 | 3.708 | 1758 | 329 | | 0.1747 |
| 2 | 4.100 | 34324 | 4049 | | 3.4100 |
| 3 | 5.208 | 5079 | 273 | | 0.3058 |
| 4 | 6.833 | 2449 | 213 | | 0.2433 |
| 5 | 7.517 | 1273 | 172 | | 0.1264 |
| 6 | 8.158 | 3314 | 332 | | 0.3292 |
| 7 | 9.475 | 928591 | 84784 | | 92.2556 |
| 8 | 12.742 | 29916 | 3427 | | 2.9722 |
| 9 | 13.725 | 1840 | 225 | | 0.1828 |
| TOTAL | | 1006542 | 93803 | | 100.0000 |

CHROMATOPAC C-R7A  CH=1  REPORT NO. = 8
CHROMATOGRAM = 1:SPPS1.C02   94/02/16  10:45:24
ANALYSIS FILE : 1 : ANALYSIS TABLE
SAMPLE : AB•629   Lot 229.402151
COLUMN : YMC Pak ODS-AM (4.6mm I.D. x 150mm) Lot. 041516478
ELUANT : 20 - 70 % CH3CN/0.1% TFA (25min)
TEMP. : 50° C        FLOW RATE : 1.0 ml/min.
DETECTOR : 220nm (0.64 AUFS)
LOAD : 10ul (conc. 0.53 mg/530μl 2M AcOH)

RESULTS OF QUANTITATIVE CALCULATION

| CH | PKNO | TIME | AREA | HEIGHT | NK | IDNO | CONC | NAME |
|---|---|---|---|---|---|---|---|---|
| 1 | 1 | 14.588 | 12783 | 1138 |   |   | 0.78 |   |
|   | 2 | 15.042 | 44299 | 4365 | V |   | 2.72 |   |
|   | 3 | 15.233 | 1572014 | 197144 | V |   | 96.5 |   |
|   |   | TOTAL | 1629096 | 202646 |   |   | 100 |   |

CHROMATOPAC C-R7A  CH=1  REPORT NO. = 7
CHROMATOGRAM = 1:SPPS1.C03   94/02/24  11:34:36
ANALYSIS FILE : 1 : ANALYSIS TABLE
SAMPLE : D•343   Lot 769.402233
COLUMN : YMC Pak CDS-AM (4.6mm I.D. x 150mm) Lot. 041516478
ELUANT : 20 - 70 % CH3CN/0.1% TFA (25min)
TEMP. : 50° C       FLOW RATE : 1.0 ml/min.
DETECTOR : 220nm (0.64 AUFS)
LOAD : 10ul (conc. 0.58 mg/580µl 0.1% TFA)

RESULTS OF QUANTITATIVE CALCULATION

| CH | PKNO | TIME | AREA | HEIGHT | NK | IDNO | CONC | NAME |
|---|---|---|---|---|---|---|---|---|
| 1 | 1 | 10.803 | 3728 | 522 | | | 0.29 | |
| | 3 | 14.317 | 32780 | 3261 | V | | 2.56 | |
| | 4 | 14.505 | 1241699 | 148761 | V | | 97.14 | |
| | | TOTAL | 1278207 | 152544 | | | 100 | |

FIG. 24  (TABLE 1)

```
[ckk-n5]
 L   S   G   R   P   A   I   V   P   D   R   E   L   L   Y   Q   E   F   D   E
Leu Ser Gly Arg Pro Ala Ile Val Pro Asp Arg Glu Leu Leu Thr Gln Glu Phe Asp Gln

[ckk-n51]
 L   S   G   R   P   A   I   V   P   D
Leu Ser Gly Arg Pro Ala Ile Val Pro Asp

[ckk-n52]
 R   E   L   L   Y   Q   E   F   D   E
Arg Glu Leu Leu Thr Gln Glu Phe Asp Gln

[ckk-n53]
 A   I   V   P   D   R   E   L   L   Y
Ala Ile Val Pro Asp Arg Glu Leu Leu Thr

[ckk-n54]
 R   P   A   I   V   P   D   R   E   L   L   Y   Q   E
Arg Pro Ala Ile Val Pro Asp Arg Glu Leu Leu Thr Gln Glu

[ckk-n55]
 P   A   I   V   P   D   R   E   L   L   Y   Q
Pro Ala Ile Val Pro Asp Arg Glu Leu Leu Thr Gln
```

FIG. 25

(TABLE 2)

```
[ckk-n6]
 V   N   Q   R   A   V   V   A   P   D   K   E   V   L   Y   E   A   F   D   E
Val Asn Gln Arg Ala Val Val Ala Pro Asp Lys Glu Val Leu Thr Glu Ala Phe Asp Gln

[ckk-n61]
 V   N   Q   R   A   V   V   A   P   D
Val Asn Gln Arg Ala Val Val Ala Pro Asp

[ckk-n62]
 K   E   V   L   Y   E   A   F   D   E
Lys Glu Val Leu Thr Glu Ala Phe Asp Gln

[ckk-n63]
 V   A   P   D   K   E   V   L   Y
Val Ala Pro Asp Lys Glu Val Leu Thr

[ckk-n64]
 R   A   V   V   A   P   D   K   E   V   L   Y   E   A
Arg Ala Val Val Ala Pro Asp Lys Glu Val Leu Thr Glu Ala

[ckk-n65]
 A   V   V   A   P   D   K   E   V   L   Y   E
Ala Val Val Ala Pro Asp Lys Glu Val Leu Thr Glu
```

FIG. 26

(TABLE 3)

```
NS5
[ckk-n3]
   C   T   T   H   H   V   S   P   D   A   D   L   I   E   A   N   L   L   W   R
   Cys Thr Thr His His Val Ser Pro Asp Ala Asp Leu Ile Gln Ala Asn Leu Leu Trp Arg

[ckk-n31]
   C   T   T   H   H   V   S   P   D   A
   Cys Thr Thr His His Val Ser Pro Asp Ala

[ckk-n32]
   D   L   I   E   A   N   L
   Asp Leu Ile Gln Ala Asn Leu

[ckk-n33]
   V   S   P   D   A   D   L   I   E   A
   Val Ser Pro Asp Ala Asp Leu Ile Gln Ala

[ckk-n34]
   H   V   S   P   D   A   D   L   I   E   A   N   L
   His Val Ser Pro Asp Ala Asp Leu Ile Gln Ala Asn Leu

[ckk-n35]
   H   V   S   P   D   A   D   L   I   E   A   N
   His Val Ser Pro Asp Ala Asp Leu Ile Gln Ala Asn
```

FIG. 27

(TABLE 4)

```
[ckk-n4]
C   T   T   H   G   K   A   Y   D   V   D   M   V   D   A   N   L   F   M   G
Cys Thr Thr His Gly Lys Ala Thr Asp Val Asp Met Val Asp Ala Asn Leu Phe Met Gly

[ckk-n41]
C   T                   A   Y   D   V
Cys Thr                 Ala Thr Asp Val

[ckk-n42]
D   M   V               K   A   Y   D                       G
Asp Met Val             Lys Ala Thr Asp                     Gly

[ckk-n43]
K   A   Y   D   M   V   D   A
Lys Ala Thr Asp Met Val Asp Ala

[ckk-n44]
H   G   K   A   Y   D   V   D   M   V   D   A   N   L
His Gly Lys Ala Thr Asp Val Asp Met Val Asp Ala Asn Leu

[ckk-n45]
G   K   A   Y   D   V   D   M   V   D   A   N
Gly Lys Ala Thr Asp Val Asp Met Val Asp Ala Asn
```

FIG. 28

(TABLE 5)

```
NS4
[ckk-n1]
 Q   E   F   D   E   M   E   E   C   A   S   H   L   P   Y   I   E   Q   G   M
Gln Glu Phe Asp Glu Met Glu Glu Cys Ala Ser His Leu Pro Tyr Ile Glu Gln Gly Met

[ckk-n11]
 Q   E   F   D   E   M   E   E   C   A
Gln Glu Phe Asp Glu Met Glu Glu Cys Ala

[ckk-n12]
 S   H   L   P   Y   I   E   Q   G   M
Ser His Leu Pro Tyr Ile Glu Gln Gly Met

[ckk-n13]
 M   E   C   A   S   H   L   P   Y
Met Glu Cys Ala Ser His Leu Pro Tyr

[ckk-n14]
 D   E   M   E   E   C   A   S   H   L   P   Y   I   E
Asp Glu Met Glu Glu Cys Ala Ser His Leu Pro Tyr Ile Glu

[ckk-n15]
 E   M   E   E   C   A   S   H   L   P   Y   I
Glu Met Glu Glu Cys Ala Ser His Leu Pro Tyr Ile
```

FIG. 29

(TABLE 6)

```
[ckk-n2]
  E   A   F   D   E   M   E   E   C   A   S   R   A   A   L   I   E   E   G   Q
  Glu Ala Phe Asp Glu Met Glu Glu Cys Ala Ser Arg Ala Ala Tyr Ile Glu Glu Gly Gln

[ckk-n21]
  E   A   F   D   E   M   E   E   C   A
  Glu Ala Phe Asp Gln Met Glu Glu Cys Ala

[ckk-n22]
  S   R   A   A   L   I   E
  Ser Arg Ala Ala Tyr Ile Glu

[ckk-n23]
  M   E   E   C   A   S   R   A   A   L
  Met Glu Glu Cys Ala Ser Arg Ala Ala Tyr

[ckk-n24]
  D   E   M   E   E   C   A   S   R   A   A   L   I   E
  Asp Gln Met Glu Glu Cys Ala Ser Arg Ala Ala Tyr Ile Glu

[ckk-n25]
  E   M   E   E   C   A   S   R   A   A   L   I
  Gln Met Glu Glu Cys Ala Ser Arg Ala Ala Tyr Ile
```

FIG. 30 (TABLE 7)

| NO. | ckk-n5 | ckk-n6 | PCR JUDGEMENT | NS4L2 JUDGEMENT | | NO. | | | | |
|-----|--------|--------|---------------|-----------------|---|-----|---|---|---|---|
| 1 | 1.382 | 4.000 | 4 | 2 | | 24 | 4.000 | 0.456 | 2 | |
| 2 | 1.715 | 4.000 | 3 | 2 | | 25 | 4.000 | 0.430 | 2 | |
| 3 | 0.724 | 4.000 | 4 | 2 | | 26 | 1.703 | 0.428 | 2 | |
| 4 | 0.577 | 4.000 | 3 | 2 | | 27 | 0.986 | 0.416 | 4 | |
| 5 | 1.887 | 4.000 | 3 | 2 | | 28 | 1.846 | 0.414 | 2 | |
| 6 | 1.888 | 3.501 | 2 | 2 | | 29 | 4.000 | 0.402 | 2 | |
| 7 | 0.852 | 3.469 | 4 | 2 | | 30 | 3.990 | 0.396 | 2 | |
| 8 | 0.387 | 3.155 | 4 | 2 | | 31 | 4.000 | 0.365 | 2 | |
| 9 | 0.373 | 2.423 | 3 | 2 x | | 32 | 2.217 | 0.350 | 2 | |
| 10 | 0.925 | 2.230 | 4 | 2 | | 33 | 1.423 | 0.346 | 2 | |
| 11 | 0.767 | 2.104 | 3 | 2 | | 34 | 4.000 | 0.340 | 2 | |
| 12 | 0.377 | 0.957 | 4 | 2 | | 35 | 3.721 | 0.337 | 2 | |
| 13 | 0.288 | 0.776 | 4 | 2 | | 36 | 3.235 | 0.333 | 2 | |
| 14 | 4.000 | 2.448 | 1 | 1 | | 37 | 3.935 | 0.327 | 2 | |
| 15 | 4.000 | 2.298 | 2 | 1 | | 38 | 4.000 | 0.326 | 2 | |
| 16 | 2.877 | 1.279 | 3 | 1 | | 39 | 0.771 | 0.322 | 2 | |
| 17 | 3.814 | 0.983 | 2 | 1 | | 40 | 1.757 | 0.317 | 2 | |
| 18 | 4.000 | 0.813 | 2 | 1 x | | 41 | 4.000 | 0.306 | 2 | |
| 19 | 1.926 | 0.728 | 4 | 1 | | 42 | 4.000 | 0.266 | 2 | |
| 20 | 1.942 | 0.689 | 5 | 1 x | | 43 | 4.000 | 0.198 | 2 | |
| 21 | 1.958 | 0.483 | 2 | 1 | | 44 | 2.825 | 0.169 | 2 | |
| 22 | 3.288 | 0.475 | 2 | 1 | | 45 | 4.000 | 0.161 | 2 | |
| 23 | 3.700 | 0.462 | 2 | 1 | | | | | | |

FIG. 31
(TABLE 8)

| NO. | ckk-n3 | ckk-n4 | PCR JUDGE-MENT | NS5 JUDGE-MENT | NO. | | | |
|---|---|---|---|---|---|---|---|---|
| 1 | 0.364 | 4.000 | 3 | 2 | 25 | 4.000 | 0.295 | 2 | 1 |
| 2 | 0.651 | 3.901 | 3 | 2 | 26 | 0.463 | 0.289 | 2 | 1 |
| 3 | 0.626 | 3.534 | 4 | 2 | 27 | 0.465 | 0.288 | 2 | 1 |
| 4 | 0.434 | 2.191 | 3 | 2 | 28 | 0.500 | 0.283 | 2 | 1 |
| 5 | 0.384 | 1.598 | 5 | 2 | 29 | 2.338 | 0.279 | 2 | 1 |
| 6 | 0.529 | 1.536 | 3 | 2 | 30 | 3.607 | 0.275 | 2 | 1 |
| 7 | 0.497 | 0.970 | 3 | 2 | 31 | 4.000 | 0.261 | 3 | 1 |
| 8 | 0.333 | 0.617 | 3 | 2 | 32 | 0.471 | 0.258 | 2 | 1 |
| 9 | 0.355 | 0.605 | 3 | 1 | 33 | 0.598 | 0.258 | 2 | 1 |
| 10 | 1.232 | 0.766 | 2 | 1 | 34 | 1.039 | 0.256 | 2 | 1 |
| 11 | 2.173 | 0.709 | 5 | 1 | 35 | 4.000 | 0.254 | 4 | 1 |
| 12 | 0.747 | 0.494 | 2 | 1 | 36 | 1.279 | 0.249 | 4 | 1 |
| 13 | 0.868 | 0.376 | 2 | 1 | 37 | 0.416 | 0.248 | 2 | 1 |
| 14 | 4.000 | 0.358 | 2 | 1 | 38 | 0.408 | 0.248 | 2 | 1 |
| 15 | 3.491 | 0.347 | 2 | 1 | 39 | 1.003 | 0.247 | 2 | 1 |
| 16 | 4.000 | 0.346 | 2 | 1 | 40 | 2.935 | 0.244 | 2 | 1 |
| 17 | 0.658 | 0.340 | 2 | 1 | 41 | 4.000 | 0.241 | 2 | 1 |
| 18 | 1.375 | 0.326 | 2 | 1 | 42 | 1.274 | 0.239 | 1 | 1 |
| 19 | 0.506 | 0.325 | 2 | 1 | 43 | 1.930 | 0.236 | 2 | 1 |
| 20 | 0.533 | 0.320 | 3 | 1 | 44 | 1.671 | 0.227 | 2 | 1 |
| 21 | 0.502 | 0.316 | 2 | 1 | 45 | 4.000 | 0.219 | 2 | 1 |
| 22 | 0.590 | 0.303 | 2 | 1 | 46 | 4.000 | 0.218 | 2 | 1 |
| 23 | 1.958 | 0.299 | 2 | 1 | 47 | 3.963 | 0.215 | 2 | 1 |
| 24 | 0.470 | 0.295 | 2 | 1 | 48 | 4.000 | 0.202 | 2 | 1 |

FIG. 32

(TABLE 9)

| NO. | ckk-n1 | ckk-n2 | PCR JUDGE-MENT | NS4L3 JUDGE-MENT |
|---|---|---|---|---|
| 1 | 0.413 | 0.797 | 4 | 2 |
| 2 | 0.247 | 0.683 | 3 | 2 |
| 3 | 1.091 | 0.205 | 1 | 1 |
| 4 | 0.643 | 0.208 | 2 | 1 |
| 5 | 2.577 | 0.219 | 1 | 1 |
| 6 | 2.453 | 0.341 | 2 | 1 |
| 7 | 0.506 | 0.257 | 2 | 1 |
| 8 | 0.711 | 0.218 | 2 | 1 |
| 9 | 0.514 | 0.270 | 2 | 1 |
| 10 | 0.488 | 0.254 | 2 | 1 |
| 11 | 2.388 | 0.235 | 2 | 1 |
| 12 | 1.318 | 0.199 | 2 | 1 |
| 13 | 0.543 | 0.265 | 2 | 1 |
| 14 | 0.664 | 0.216 | 2 | 1 |
| 15 | 0.776 | 0.225 | 5 | 1 |
| 16 | 4.000 | 0.189 | 2 | 1 |
| 17 | 0.750 | 0.209 | 2 | 1 |
| 18 | 4.000 | 0.274 | 2 | 1 |
| 19 | 3.526 | 0.291 | 2 | 1 |
| 20 | 2.997 | 0.222 | 2 | 1 |
| 21 | 3.514 | 0.334 | 2 | 1 |
| 22 | 1.310 | 0.248 | 2 | 1 |
| 23 | 0.329 | 0.215 | 2 | 1 |
| 24 | 0.469 | 0.229 | 4 | 1 |
| 25 | 1.959 | 0.359 | 2 | 1 |
| 26 | 4.000 | 0.276 | 2 | 1 |
| 27 | 0.610 | 0.286 | 2 | 1 |
| 28 | 4.000 | 0.239 | 2 | 1 |

FIG. 33
(TABLE 10)

| NO. | ckk-c1 | ckk-c2 | PCR JUDGE-MENT | core JUDGE-MENT | NO. | | | |
|---|---|---|---|---|---|---|---|---|
| 1 | 2.196 | 4.000 | 3 | 2 | 22 | 4.000 | 1.373 | 2 | 1 |
| 2 | 1.644 | 3.657 | 3 | 2 | 23 | 4.000 | 1.187 | 2 | 1 |
| 3 | 0.535 | 3.505 | 4 | 2 | 24 | 4.000 | 1.174 | 5 | 1 |
| 4 | 0.786 | 3.374 | 4 | 2 | 25 | 4.000 | 1.167 | 2 | 1 |
| 5 | 0.456 | 3.085 | 3 | 2 | 26 | 1.562 | 0.954 | 2 | 1 |
| 6 | 0.421 | 2.916 | 3 | 2 | 27 | 1.818 | 0.813 | 2 | 1 |
| 7 | 0.567 | 2.679 | 4 | 2 | 28 | 2.191 | 0.708 | 2 | 1 |
| 8 | 0.801 | 2.292 | 4 | 2 | 29 | 1.860 | 0.702 | 2 | 1 |
| 9 | 0.963 | 1.768 | 4 | 2 | 30 | 3.669 | 0.684 | 2 | 1 |
| 10 | 1.034 | 1.739 | 4 | 2 | 31 | 4.000 | 0.626 | 2 | 1 |
| 11 | 0.511 | 1.518 | 4 | 2 | 32 | 4.000 | 0.608 | 2 | 1 |
| 12 | 0.694 | 1.503 | 4 | 2 | 33 | 1.758 | 0.546 | 2 | 1 |
| 13 | 0.958 | 1.496 | 3 | 2 | 34 | 1.777 | 0.543 | 2 | 1 |
| 14 | 0.874 | 1.411 | 2 | 2 | 35 | 4.000 | 0.516 | 2 | 1 |
| 15 | 0.447 | 1.089 | 3 | 2 | 36 | 2.591 | 0.448 | 2 | 1 |
| 16 | 0.567 | 1.024 | 3 | 2 | 37 | 3.735 | 0.440 | 2 | 1 |
| 17 | 0.643 | 0.994 | 3 | 2 | 38 | 0.677 | 0.439 | 2 | 1 |
| 18 | 0.386 | 0.866 | 3 | 2 | 39 | 1.249 | 0.435 | 5 | 1 |
| 19 | 0.409 | 0.775 | 4 | 2 | 40 | 0.891 | 0.389 | 2 | 1 |
| 20 | 0.379 | 0.573 | 5 | 2 | 41 | 1.657 | 0.362 | 5 | 1 |
| 21 | 3.825 | 1.626 | 2 | 1 | 42 | 0.456 | 0.295 | 2 | 1 |

FIG. 34

| HCV Case | N | NS4(40) NUMBER OF JUDGEMENTS | NS4(20) NUMBER OF JUDGEMENTS |
|---|---|---|---|
| CAH | 83 | 69 | 52 |
| CPH | 17 | 15 | 13 |

FIG. 36

NUMBER OF JUDGEMENTS CORRESPONDING TO ANTIGENIC REGIONS

|  | NS4 | NS5 | core | N |
|---|---|---|---|---|
| CH2A | 40 | 18 | 8 | 48 |
| CH2B | 29 | 12 | 6 | 36 |
| CPH | 15 | 11 | 5 | 17 |

FIG. 35

| CH2A TYPE | N=48 | HCV TYPE SUBTYPE | | | IFN | | |
|---|---|---|---|---|---|---|---|
| | | 2 | 3 | 4 | N | P | C |
| 1 | | 26/31 | 4/31 | 1/31 | 19/31 | 3/31 | 9/31 |
| 2 | | 4/12 | 8/12 | 0/12 | 2/12 | 4/12 | 6/12 |
| 1+2 | | 0 | 0 | 0 | | | |
| - | | 3/5 | 1/5 | 1/5 | 3/5 | 0/5 | 2/5 |

| CH2B TYPE | N=36 | HCV TYPE SUBTYPE | | | IFN | | |
|---|---|---|---|---|---|---|---|
| | | 2 | 3 | 4 | N | P | C |
| 1 | | 24/24 | 0/24 | 0/24 | 19/24 | 4/24 | 1/24 |
| 2 | | 0/7 | 7/7 | 0/7 | 1/7 | 1/7 | 5/7 |
| 1+2 | | 0/1 | 1/1 | 0/1 | 1/1 | 0/1 | 0/1 |
| - | | 3/4 | 1/4 | 0/4 | 2/4 | 1/4 | 1/4 |

| CPH TYPE | N=17 | HCV TYPE SUBTYPE | | | IFN | | |
|---|---|---|---|---|---|---|---|
| | | 2 | 3 | 4 | N | P | C |
| 1 | | 11/11 | 0/11 | 0/11 | 6/11 | 0/11 | 5/11 |
| 2 | | 1/4 | 3/4 | 0/4 | 1/4 | 0/4 | 3/4 |
| 1+2 | | 1/1 | 0/1 | 0/1 | 0/1 | 0/1 | 1/1 |
| - | | 0/1 | 0/1 | 1/1 | 0/1 | 1/1 | 0/1 | ns
ANTIGENIC PEPTIDE COMPOUND AND IMMUNOASSAY

TECHNICAL FIELD

The present invention relates to an antigenic peptide compound and an immunoassay which are useful for measuring an antibody relating to HCV (hepatitis C virus).

BACKGROUND ART

Various kinds of viruses exist on the earth, and some of them are pathogens. For example, it is known that a hepatitis virus as a cause of viral hepatitis is transmissible at the time of blood transfusion, injection, childbirth, etc.

The blood transfusion is one of the important measures for maintaining the life of a human being. However, there have heretofore been reported a large number of cases such that the blood transfusion causes viral hepatitis. In general, the viral hepatitis is classified into hepatitis A, hepatitis B and non-A non-B hepatitis.

Conventionally, it is known that hepatitis B virus (HBV) also causes viral hepatitis at the time of the blood transfusion. In recent years, a diagnostic reagent for detecting the presence of the HBV has been developed, and it has become possible to easily confirm the presence of the HBV prior to the blood transfusion. Accordingly, the HBV infection of a human being due to the blood transfusion has entirely been prevented. On the other hand, it is also known the existence of another hepatitis (non-A non-B hepatitis) which is clearly viral, but is different from the hepatitis A caused by hepatitis A virus (HAV) and also different from the hepatitis B caused by HBV, while the HAV and HBV have heretofore been considered as the causes of hepatitis. However, it has heretofore been considered to be difficult to confirm the cause (virus) of such non-A non-B hepatitis.

In 1989, Choo, Q-L. et al. (Science, 244, 359–362, 1989) and Kuo ,G. et al. (Science, 244, 362–364, 1989) proved the existence of the non-A non-B hepatitis virus. This hepatitis virus was named "HCV" (hepatitis C virus). It has heretofore been reported that the HCV is selectively transmissible to a human being and a chimpanzee.

The above-mentioned paper describes the following experiments. That is, a preparation of blood coagulation Factor VIII which was the same as the preparation which had caused the non-A non-B hepatitis when administered to a patient, was administered to a Chimpanzee-No. 1 thereby to cause non-A non-B hepatitis. Further, a preparation extracted from the liver of the above Chimpanzee-No. 1 was similarly administered to a Chimpanzee-No. 2 thereby to cause non-A non-B hepatitis, and thereafter, the blood plasma of this Chimpanzee-No. 2 was extracted. The resultant blood plasma of the Chimpanzee-No. 2 was further administered to a Chimpanzee-No. 3, whereby the occurrence of non-A non-B hepatitis was confirmed. The resultant blood plasma which had confirmedly cause the disease, was subjected to a concentration procedure for virus particles (Bradley, D. W. et al.; Gastroenterology, 88: 773–779, 1989) under the assumption that the virus to be obtained was flavivirus, whereby RNA of the virus was extracted. Then, cDNA was synthesized on the basis of the thus obtained RNA, and a λgt11 library was prepared. With respect to the resultant λgt11 library, immunoscreening was conducted by using the blood serum of a convalescent chimpanzee or the blood serum of a chronic non-A non-B hepatitis patient, thereby to select a reactive clone. As a result, it was confirmed that only the clone named "5-1-1" was a cDNA fragment originated from HCV.

The above-mentioned procedure is also described in Japanese Patent Publication (KOKOKU) No. Hei 2-500880 (500880/1990), wherein the genetic sequence thereof is also shown. In addition, a genetic sequence of the HCV was also reported in Japan (Journal of Virology, 65(3), 1105–1113, 1991).

In the meeting of ACTA HEPATOLOGICA JAPONICA in June of 1990, a genetic sequence of the HCV structural region was shown by Okamoto of Jichi Medical School et al. (Proceedings of the 26th Meeting of ACTA HEPATOLOGICA JAPONICA in 1990). In the meeting of Japan Cancer Society in July of 1990, a genetic sequence of the HCV structural region was shown (Proceedings of the 49th meeting of Japan Cancer Society in 1990) similarly as in the above-mentioned publication by Okamoto et al. When these publications are compared with each other, it has been found that substantially no mutation is observed in the HCV core region, but a somewhat difference is recognized between these publications with respect to the HCV envelope region.

Thereafter, there has been proposed an antibody diagnosis using the core antigen of the HCV structural region in combination with an antigenic site of the HCV non-structural region (Rinsho-Byori (The Japanese Journal of Clinical Pathology), 40(12), 1245–1251, 1992). When such an antibody diagnosis is used, it has become possible to conduct an almost perfect screening for an HCV antibody-detected person.

On the other hand, in parallel with the above HCV diagnosis, a treatment for hepatitis C using interferon has been initiated. In this treatment, it has been found that the effect of the interferon treatment varies according to the kind of the genetic type (genotype) of the HCV.

The classification of the genotype has been proposed by Okamoto H. in KAN TAN SUI, 24, 7–14 (1992), and the genotypes are classified into Type-I (Proc. Natl. Acad. Sci. USA, 88, 2451–2455, 1991), Type-II (Journal of Virology, 65(3), 1105–1113, 1991), Type-III (Journal of General Virology, 72, 2697–2704, 1991), and Type-IV (Virology, 188, 331–341, 1992). In the meeting of ACTA HEPATOLOGICA JAPONICA held in June of 1993, it was reported that the interferon treatment for genotype-I and -II (interferon treatment: effective in 20% of individuals tested) was lower than that for genotype-III and -IV (interferon treatment: effective in 80% of individuals tested) (Proceedings of the 29th Meeting of ACTA HEPATOLOGICA JAPONICA, page 55, 1993).

In many cases, the administration of the interferon produces a strong side effect such as alopecia and fever, and the load thereof to the patient is heavy. Therefore, the determination of the HCV genotype prior to the treatment is extremely important in view of the prediction of the effect of the interferon administration. However, in the conventional method of determining the genotype, the HCV RNA is extracted from the specimen of a patient, cDNA complementary to the resultant RNA is synthesized, the cDNA is amplified by a PCR (polymerase chain reaction) method, and a band corresponding to the thus amplified cDNA is identified by use of electrophoresis, thereby to determine the genotype. Since such a procedure includes complicated steps and usually lasts for 48 hours or more, it requires a long period of time and a high cost.

On the other hand, it has been reported that the HCV antibodies in the blood sera of patients can be classified into two types by using an antigen (including about 300 amino acids) which has been prepared by a genetic recombination technique (KAN TAN SUI, 22, 883–889, 1991). However, this classification is not necessarily sufficient in view of the correspondence thereof with the above-mentioned genotype, which is important in determining the interferon treatment.

As described above, the administration of the interferon requires a high cost, and further, the determination of the above-mentioned genotype, which is a prerequisite for the interferon administration, has a disadvantage such that the determination per se also requires a high cost. If the genotype of the HCV can be determined easily prior to the interferon administration, it becomes possible to easily predict the effect of the interferon administration so as to properly design the method of administrating the interferon and a guideline for the treatment using the same. In addition, it becomes possible to reduce the mental, physical and economic load to the patient. Accordingly, there has eagerly been desired a simple method of determining the HCV genotype.

Accordingly, an object of the present invention is to provide an antigen for measuring an HCV antibody, which enables simple determination of the HCV antibody wherein the genotype-I and genotype-II can be distinguished from the genotype-III and genotype-IV.

DISCLOUSRE OF INVENTION

As a result of earnest study, the present inventor has found that the determination of an HCV antibody type (serotype) using a specific amino acid sequence based on the an HCV antigenic site (a sequence comprising at least six amino acids) not only enables simple discrimination of genotype-I and -II of HCV from the genotype-III and -IV, but also effectively suppress a cross reaction or non-specific reaction which can occur along with an antigen-antibody reaction, whereby such determination is extremely effective in achieving the above-mentioned object.

The antigenic peptide compound according to the present invention is based on the above discovery, and specifically comprises: a sequence which comprises at least six sequential amino acids and is included in an amino acid sequence represented by the following formula (1):

Leu-Ser-Gly-Arg-Pro-Ala-Ile-Val-Pro-Asp-Arg-Glu-Val-Leu-Tyr-Gln-Glu-Phe-Asp-Glu . . . (SEQ ID NO: 1) (ckk-n5)

The present invention also provides an antigenic peptide compound, comprising a sequence which comprises at least six sequential amino acids and is included in an amino acid sequence represented by the following formula (2):

Val-Asn-Gln-Arg-Ala-Val-Val-Ala-Pro-Asp-Lys-Glu-Val-Leu-Tyr-Glu-Ala-Phe-Asp-Glu . . . (SEQ ID NO: 2) (ckk-n6)

The present invention further provides an antigenic peptide compound, comprising a sequence which comprises at least six sequential amino acids and is included in an amino acid sequence represented by the following formula (3):

Cys-Thr-Thr-His-His-Val-Ser-Pro-Asp-Ala-Asp-Leu-Ile-Glu-Ala-Asn-Leu-Leu-Trp-Arg . . . (SEQ ID NO: 3) (ckk-n3)

The present invention further provides an antigenic peptide compound, comprising a sequence which comprises at least six sequential amino acids and is included in an amino acid sequence represented by the following formula (4):

Cys-Thr-Thr-His-Gly-Lys-Ala-Tyr-Asp-Val-Asp-Met-Val-Asp-Ala-Asn-Leu-Phe-Met-Gly . . . (SEQ ID NO: 4) (ckk-n4)

The present invention further provides an antigenic peptide compound, comprising a sequence which comprises at least six sequential amino acids and is included in an amino acid sequence represented by the following formula (5):

Gln-Glu-Phe-Asp-Glu-Met-Glu-Glu-Cys-Ala-Ser-His-Leu-Pro-Tyr-Ile-Glu-Gln-Gly-Met . . . (SEQ ID NO: 5) (ckk-n1)

The present invention further provides an antigenic peptide compound, comprising a sequence which comprises at least six sequential amino acids and is included in an amino acid sequence represented by the following formula (6):

Glu-Ala-Phe-Asp-Glu-Met-Glu-Glu-Cys-Ala-Ser-Arg-Ala-Ala-Leu-Ile-Glu-Glu-Gly-Gln . . . (SEQ ID NO: 6) (ckk-n2)

The present invention further provides an antigenic peptide compound, comprising a sequence which comprises at least six sequential amino acids and is included in an amino acid sequence represented by the following formula (7):

Gly-Arg-Arg-Gln-Pro-Ile-Pro-Lys-Ala-Arg-Arg-Pro-Glu-Gly-Arg-Thr-Trp-Ala-Gln-Pro . . . (SEQ ID NO: 7)

The present invention further provides an antigenic peptide compound, comprising a sequence which comprises at least six sequential amino acids and is included in an amino acid sequence represented by the following formula (8):

Gly-Arg-Arg-Gln-Pro-Ile-Pro-Lys-Asp-Arg-Arg-Ser-Thr-Gly-Lys-Ser-Trp-Gly-Lys-Pro . . . (SEQ ID NO: 8)

The present invention further provides an antigenic peptide compound, comprising a sequence which comprises at least six sequential amino acids and is included in an amino acid sequence represented by the following formula (9):

Ile-Ile-Leu-Ser-Gly-Arg-Pro-Ala-Ile-Val-Pro-Asp-Arg-Glu-Leu-Leu-Tyr-Gln-Glu-Phe-Asp-Glu-Met-Glu-Glu-Cys-Ala-Ser-His-Leu-Pro-Tyr-Ile-Glu-Gln-Gly-Met-Gln-Leu-Ala . . . (SEQ ID NO: 9) (ckk-n1(40))

(One character description: IILSG RPAIV PDREL LYQEF DEMEE CASHL PYIEQ GMQLA)

The present invention further provides an antigenic peptide compound, comprising a sequence which comprises at least six sequential amino acids and is included in an amino acid sequence represented by the following formula (10):

Leu-His-Val-Asn-Gln-Arg-Ala-Val-Val-Ala-Pro-Asp-Lys-Glu-Val-Leu-Tyr-Glu-Ala-Phe-Asp-Glu-Met-Glu-Glu-Cys-Ala-Ser-Arg-Ala-Ala-Leu-Ile-Glu-Glu-Gly-Gln-Arg-Ile-Ala . . . (SEQ ID NO: 10) (ckk-n2(40))

(One character description: LHVNQ RAVVA PDKEV LYEAF DEMEE CASRA ALIEE GQRIA)

The present invention further provides an immunological method of measuring an HCV antibody, comprising: fixing any of the antigenic peptides represented by the above formulas (1) to (10) to a carrier; binding an HCV antibody in a specimen to the peptide by utilizing an antigen-antibody reaction; and binding a labelled ligand to the HCV antibody by utilizing an antigen-antibody reaction, thereby to measure the HCV antibody in the specimen.

Herein, "ligand" refers to a substance (such as antibody and/or antigen) having a specific binding affinity to an antigen and/or antibody.

In the above-mentioned conventional determination of genotype, the type of HCV is determined by utilizing the sequence of the HCV gene per se. On the other hand, in the present invention, the type of HCV is determined by utilizing the type of an antibody (serotype) corresponding to an antigenic site peculiar to the HCV. Such determination of the antibody type according to the present invention may be conducted within a much shorter period of time as compared with the period of time required for the conventional genotype determination (extraction of HCV RNA→synthesis of cDNA→amplification of the cDNA by PCR method→identification of the amplified band using electrophoresis). In addition, the operation steps constituting the antibody type determination are simple. As a result, according to the present invention, there may be provided a method of simply determining the HCV type (genotype) at a low cost.

In addition, in the present invention, the cross reaction or non-specific reaction which can occur along with an antigen-antibody reaction is effectively suppressed, as compared with that in the case of the conventional method of determining the serum type by utilizing an antigen comprising about 300 amino acids.

BRIEF DESCRIPTION OF DRAWINGS

FIG. 24 (Table 1) is a table showing the amino acid sequences included in the peptide compound (1)(SEQ ID NOS: 1 and 13–17 are shown in this figure).

FIG. 25 (Table 2) is a table showing the amino acid sequences included in the peptide compound (2)(SEQ ID NOS: 2 and 18–22 are shown in this figure).

FIG. 26 (Table 3) is a table showing the amino acid sequences included in the peptide compound (3)(SEQ ID NOS: 3 and 23–27 are shown in this figure).

FIG. 27 (Table 4) is a table showing the amino acid sequences included in the peptide compound (4)(SEQ ID NOS: 4 and 28–32 are shown in this figure).

FIG. 28 (Table 5) is a table showing the amino acid sequences included in the peptide compound (5)(SEQ ID NOS: 5 and 33–37 are shown in this figure).

FIG. 29 (Table 6) is a table showing the amino acid sequences included in the peptide compound (6)(SEQ ID NOS: 6 and 38–42 are shown in this figure).

FIG. 30 (Table 7) is a table obtained by summarizing the results of serotype determination obtained in Examples 4 and 5.

FIG. 31 (Table 8) is a table obtained by summarizing the results of serotype determination obtained in Example 6.

FIG. 32 (Table 9) is a table obtained by summarizing the results of serotype determination obtained in Example 7.

FIG. 33 (Table 10) is a table obtained by summarizing the results of serotype determination obtained in Example 8.

FIG. 34 (Table 11) is a table obtained by summarizing the results of serotype determination obtained in Example 9.

FIG. 35 (Table 12) is a table obtained by summarizing the results of serotype determination obtained in Example 10.

FIG. 36 (Table 13) is a table obtained by summarizing the results of serotype determination obtained in Example 10 by use of an NS-4 region antigenic peptide, an NS-5 region antigenic peptide, and a core region antigenic peptide.

BEST MODE FOR CARRYING OUT THE INVENTION

Figure 1:
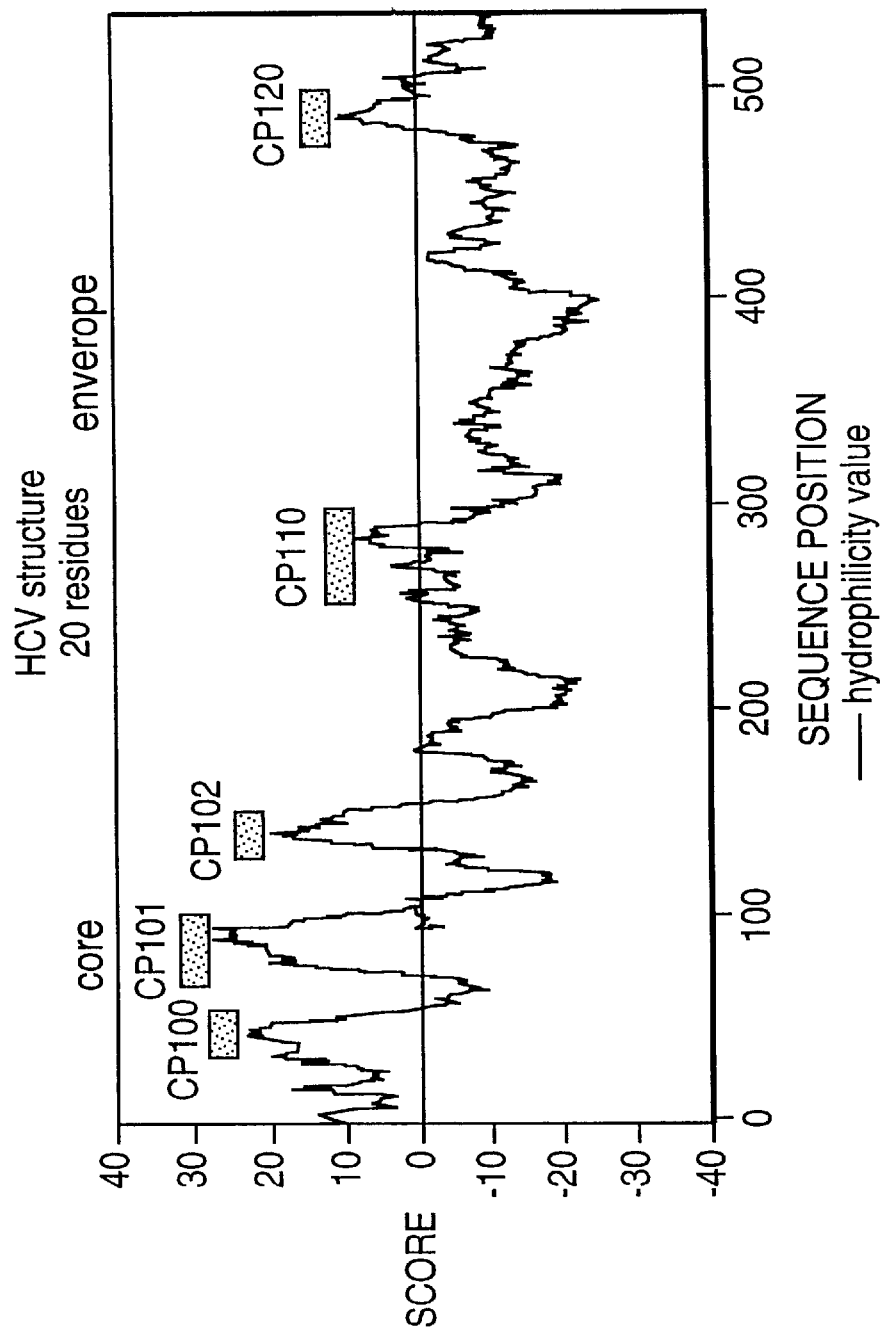
FIG. 1 is a graph showing the results obtained by calculating the "Hydrophilicity Value" in Example 1 with respect to the core region of HCV.

Hereinbelow, the present invention will be described in detail with reference to the accompanying drawings as desired.

In the description of the amino acid sequences in the present specification, the respective amino acids constituting an amino acid sequence are described in a direction of from the N-terminal amino acid (left end) toward the C-terminal amino acid (right end). For example, in the following amino acid sequence (1), "Leu" is the N-terminal, and "Glu" is the C-terminal. (One-character description and three-character description of amino acids)

| <Abbrev.> | | <Name> | <Abbrev.> | | <Name> |
|---|---|---|---|---|---|
| Asp | D | aspartic acid | Val | V | valine |
| Asn | N | asparagine | Met | M | methionine |
| Thr | T | threonine | Ile | I | isoleucine |
| Ser | S | serine | Leu | L | leucine |
| Glu | E | glutamic acid | Tyr | Y | tyrosine |
| Gln | Q | glutamine | Phe | F | phenylalanine |
| Pro | P | proline | Trp | W | tryptophan |
| Gly | G | glycine | Lys | K | lysine |
| Ala | A | alanine | His | H | histidine |
| Cys | C | cysteine | Arg | R | arginine |

(Antigenic peptide compound)

The antigenic peptide compound according to the present invention is a peptide compound which has a sequence included in the following formula (1) or (2) having twenty (20) amino acids, and includes a sequence of at least 6 (six) sequential amino acids.

Leu-Ser-Gly-Arg-Pro-Ala-Ile-Val-Pro-Asp-Arg-Glu-Val-Leu-Tyr-Gln-Glu-Phe-Asp-Glu . . . (SEQ ID NO: 1)
(ckk-n5; NS-4L2-1, corresponding to NS-4 region)
(one-character description: LSGRPAIVPDREVLYQEFDE)
Val-Asn-Gln-Asp-Arg-Ala-Val-Val-Ala-Pro-Asp-Lys-Glu-Val-Leu-Tyr-Glu-Ala-Phe-Asp . . . (SEQ ID NO: 2)
(ckk-n6; NS-4L2-2, corresponding to NS-4 region)
(one-character description: VNQDRAVVAPDKEVLYEAFD)

According to the present inventor's discovery, any of sequences which have various lengths, constitute the sequence represented by the above formula (1) or (2), and include at least sequential six amino acids may preferably be used as an antigen, similarly as the peptide (1) and/or (2).

Specific examples of such amino acid sequences having various lengths (including amino acids of not less than 6 and not more than 20) which are included in the above peptide compound (1), may comprise those as shown in FIG. 24 (Table 1).

In addition, specific examples of such amino acid sequences having various lengths (including amino acids of not less than 6 and not more than 20) which are included in the above peptide compound (2), may comprise those as shown in FIG. 25 (Table 2).

According to the present inventor's discovery, any of peptides (including 21 or more amino acids) which comprise the sequence represented by the above formula (1) or (2) may preferably be used as an antigen, similarly as the peptide (1) or (2). The number of the amino acids constituting such a peptide may preferably be 40 or less when the peptide is chemically synthesized; and may preferably be 100 or less when the peptide is synthesized by using a recombinant technique.

The method of obtaining the above-mentioned antigenic peptides (peptide compounds including six or more amino acids) is not particularly limited. The peptide may be synthesized by using a chemical method, or may be produced by using a genetic engineering technique (for example, genetic recombinant technique, i.e., recombinant method). When a chemical technique is used, it is preferred to link the respective amino acids by use of a solid-phase technique, in view of easiness in the purification of an intermediate product, etc. It is further preferred to synthesize the peptide by means of an automatic peptide synthesizing apparatus (e.g., "430 A" Peptide Synthesizer mfd. by Applied Bio-Systems Co.).

(Confirmation of antigenicity of antigenic peptide)

The sequences of the above peptides (1) and (2) have been discovered on the basis of the "extraction" of an antigenic site from the amino acid sequence of NS-4 region of HCV (as described in Example 1 appearing hereinafter). Further, the present inventor has investigated the HCV genotype by use of an enzyme immunoassay technique (ELISA or EIA) using these peptides (1) and (2), and has confirmed the specificity of such a technique by using specimens of patients, the HCV genotypes of which have separately been identified (as described in Examples 4 and 5 appearing hereinafter).

(Other antigenic peptides)

By use of the above-mentioned peptide (1) and (2) (both of which are sequences corresponding to the NS-4 region of HCV), it is possible to determine the serotype as descried hereinafter. In view of an increase in the accuracy in the serotype determination, or in view of an expansion in the applicable scope of the serotype determination, it is preferred to use the above-mentioned peptide (1) and/or (2) in combination with another antigenic peptide. As such "other antigenic peptide", the following peptides (3) to (10) are usable.

Cys-Thr-Thr-His-His-Val-Ser-Pro-Asp-Ala-Asp-Leu-Ile-Glu-Al-Asn-Leu-Leu-Trp-Arg . . . (SEQ ID NO: 3)
(ckk-n3; NS5L2-1, corresponding to NS-5 region)
(One-character description: CTTHHVSPDADLIEANLLWR)

Cys-Thr-Thr-His-Gly-Lys-Ala-Tyr-Asp-Val-Asp-Met-Val-Asp-Ala-Asn-Leu-Phe-Met-Gly . . . (SEQ ID NO: 4)
(ckk-n4; NS5L2-2, corresponding to NS-5 region)
(One-character description: CTTHGKAYDVDMVDANLFMG)

Gln-Glu-Phe-Asp-Glu-Met-Glu-Glu-Cys-Ala-Ser-His-Leu-Pro-Tyr-Ile-Glu-Gln-Gly-Met . . . (SEQ ID NO: 5)
(ckk-n1; NS-4L3-1, corresponding to NS-4 region)
(One-character description: QEFDEMEECA SHLPYIEQGM)

Glu-Ala-Phe-Asp-Glu-Met-Glu-Glu-Cys-Ala-Ser-Arg-Ala-Ala-Leu-Ile-Glu-Glu-Gly-Gln . . . (SEQ ID NO: 6)
(ckk-n2; NS-4L32, corresponding to NS-4 region)
(One-character description: EAFDEMEECASRAALIEEGQ)

Gly-Arg-Arg-Gln-Pro-Ile-Pro-Lys-Ala-Arg-Arg-Pro-Glu-Gly-Arg-Thr-Trp-Ala-Gln-Pro . . . (SEQ ID NO: 7)
(ckk-c1; core-1, corresponding to core region)
(One-character description: GRRQPIPKARRPEGRTWAQP)

Gly-Arg-Arg-Gln-Pro-Ile-Pro-Lys-Asp-Arg-Arg-Ser-Thr-Gly-Lys-Ser-Trp-Gly-Lys-Pro . . . (SEQ ID NO: 8)
(ckk-c2; core-2, corresponding to core region)
(One-character description: GRRQPIPKDRRSTGKSWGKP)

Ile-Ile-Leu-Ser-Gly-Arg-Pro-Ala-Ile-Val-Pro-Asp-Arg-Glu-Leu-Leu-Tyr-Gln-Glu-Phe-Asp-Glu-Met-Glu-Glu-Cys-Ala-Ser-His-Leu-Pro-Tyr-Ile-Glu-Gln-Gly-Met-Gln-Leu-Ala . . . (SEQ ID NO: 9)
(ckk-n1(40), corresponding to NS-4 region)
(One-character description:
IILSG RPAIV PDREL LYQEF DEMEE CASHL PYIEQ GMQLA)

Leu-His-Val-Asn-Gln-Arg-Ala-Val-Val-Ala-Pro-Asp-Lys-Glu-Val-Leu-Tyr-Glu-Ala-Phe-Asp-Glu-Met-Glu-Glu-Cys-Ala-Ser-Arg-Ala-Ala-Leu-Ile-Glu-Glu-Gly-Gln-Arg-Ile-Ala . . . (SEQ ID NO: 10)
(ckk-n2(40), corresponding to NS-4 region)
(One-character description:
LHVNQ RAVVA PDKEV LYEAF DEMEE CASRA ALIEE GQRIA)

With respect to the above peptides (3) to (10), it is possible to confirm the antigenicity thereof, to prepare the peptides, etc., in the same manner as in the case of the peptides (1) and (2) corresponding to the NS-4 region.

According to the present inventor's discovery, any of sequences which have various lengths, constitute the sequence represented by the above formulas (3) to (10), and includes at least six sequential amino acids may preferably be used as an antigen, similarly as each of the peptides (3), (4), (5), (6), (7), (8), (9) and/or (10)).

Specific examples of such amino acid sequences having various lengths (including amino acids of not less than 6 and not more than 20) which are included in the above peptide compound (3), may comprise those as shown in FIG. 26 (Table 3).

Specific examples of such amino acid sequences having various lengths (including amino acids of not less than 6 and not more than 20) which are included in the above peptide compound (4), may comprise those as shown in FIG. 27 (Table 4).

Specific examples of such amino acid sequences having various lengths (including amino acids of not less than 6 and not more than 20) which are included in the above peptide compound (5), may comprise those as shown in FIG. 28 (Table 5).

Further, specific examples of such amino acid sequences having various lengths (including amino acids of not less than 6 and not more than 20) which are included in the above peptide compound (6), may comprise those as shown in FIG. 29 (Table 6).

According to the present inventor's discovery, any of peptides (including 21 or more amino acids) which comprise any of the sequences represented by the above formulas (3) to (10) may preferably be used as an antigen, similarly as each of the peptides (3) to (10). The number of amino acids constituting such a peptide may preferably be 40 or less when the peptide is chemically synthesized; and may preferably be 100 or less when the peptide is synthesized by using a recombinant technique.

According to the present inventor's discovery, when any of the above peptides (1) to (10) is used as an antigen by itself, in view of the accuracy in the serotype determination, the order of preference in the use thereof as an antigen is as follows. In the description in this portion, the peptides (1) and/or (2) are inclusively referred to as "NS-4-1"; the peptides (3) and/or (4) are inclusively referred to as "NS-5"; the peptides (5) and/or (6) are inclusively referred to as "NS-4-2"; the peptides (9) and/or (10) are inclusively referred to as "NS-4-40";

and the peptides (7) and/or (8) are inclusively referred to as "core".

Preference order: NS-4-1>NS-5>NS-4-2>core

On the other hand, when at least two kinds of the above peptides NS-4-1, NS-5, NS-4-2, and core are used in combination, the order of preference in the use thereof as an antigen is as follows, in view of the accuracy in the serotype determination.

Preference order: (NS-4-1+NS-5)>(NS-4-2+NS-5)>(NS-4-1+core)>(NS-4-2+core)>(NS-5+core)

Further, when at least three kinds of the above peptides NS-4-1, NS-5, NS-4-2, and core are used in combination, the order of preference in the use thereof as an antigen is as follows, in view of the accuracy in the serotype determination.

Preference order: (NS-4-1+NS-5+core)>(NS-4-2+NS-5+core)

The above-mentioned peptide "NS-4-40" (number of amino acids=40) may preferably be used instead of the "NS-4-1" in the above combinations. In such a case wherein the "NS-4-40" is used, a higher effectiveness in the determination (=number of specimens wherein the determination is successful)/(total number of specimens subjected to the determination) may be obtained as compared with that in a case wherein the "NS-4-1" is used.
(Method of measuring HCV antibody)

By utilizing the specific affinity of the above antigenic peptide to an HCV antibody, the HCV antibody in a sample or specimen may be measured immunologically. The immunological measuring method to be used in the present invention is not particularly limited, but it is possible to utilize any of known immunoassay methods without particular limitation. Specific examples of such immunoassay methods may include: enzyme immunoassay, radioimmunoassay (RIA) fluorescence immunoassay (FIA), etc. In these immunoassay techniques, any of known procedures (such as competitive method, double-antibody method, and sandwich method) may be used without particular limitation. With respect to these known measuring techniques, corresponding papers (e.g., "Enzyme Immunoassay" (3rd edition) written by Eiji Ishikawa, pages 180 et seq., published by Igaku Shoin, with respect to EIA) may be referred to.

According to the present invention, an HCV antibody may be immunologically measured by use of the above-mentioned antigenic peptide, whereby the kind (serotype) of the HCV antibody contained in a specimen may be determined (For example, as described hereinbelow, it is possible to determine whether the serotype of the HCV antibody is classified into group-I or group-II). As described hereinbelow, the group-I of HCV serotype corresponds to the HCV genotype-I and -II; and the group-II of HCV serotype corresponds to the HCV genotype-III and -IV. Accordingly, it is possible to easily determine the HCV genotype.

In the above immunoassay, as desired, it is possible that the antigenic peptide is attached or solid phase-fixed to a carrier (or support), and the kind of the antibody against the HCV antigen (i.e., serotype of HCV) is determined by utilizing the specific affinity of the antigenic peptide to the HCV antibody. Specific examples of the carrier or support to be used for such a purpose may include: bovine serum albumin (BSA), a polypeptide preferably having a molecular weight of about $5\times10^4$ to $10\times10^4$, wells of a micro-plate, a polystyrene ball (or polystyrene bead) preferably having a diameter of about 0.1 μm to 6 mm, etc.

As described hereinabove, the above peptides (1) to (10) may suitably be used for the measurement of an HCV antibody, and may also be used for an antigen or immunogen for producing a vaccine for HCV. For example, such a vaccine may be prepared by using a genetic engineering technique (recombinant technique).

Hereinbelow, the present invention will be described in more detail with reference to Examples.

EXAMPLE 1

(Identification of antigenic site by use of Hydrophilicity Value)

First, the amino acid sequences of a non-structural region and a structural region of HCV were determined, on the basis of the sequence of the antigenic peptide synthesized in Geoffrey RS; Nature, 302, 490–495 (1983) and the genetic sequence of HCV (Proceedings of 26th Meeting of ACTA HEPATOLOGICA JAPONICA, 1990; Proceedings of 49th Meeting of Japan Cancer Society, 1990; Proc. Natl. Acad. Sci. USA, 88, 2451–2455, 1991; Journal of Virology, 65(3), 1105–1113, 1991; Journal of General Virology, 72, 2697–2704, 1991; and Virology, 188, 331–341, 1992).

On the basis of the thus determined amino acid sequence, the antigenic site thereof was evaluated by using a method described in Hopp TP; Proc. Natl. Acad. Sci. 78, 3824–3828 (1981). More specifically, the evaluation was conducted in the following manner by using the above "Hydrophilicity Value" of amino acids.

Based on the thus determined amino acid sequence constituting HCV, the Hydrophilicity Values of respective sequential six amino acids were summed up. Such calculations were conducted with respect to all the regions of the amino acid sequences of HCV, thereby to calculate the strength of their hydrophilic properties and hydrophobic properties The region showing a high hydrophilic property was treated as a site showing an antigenicity.

Figure 2:
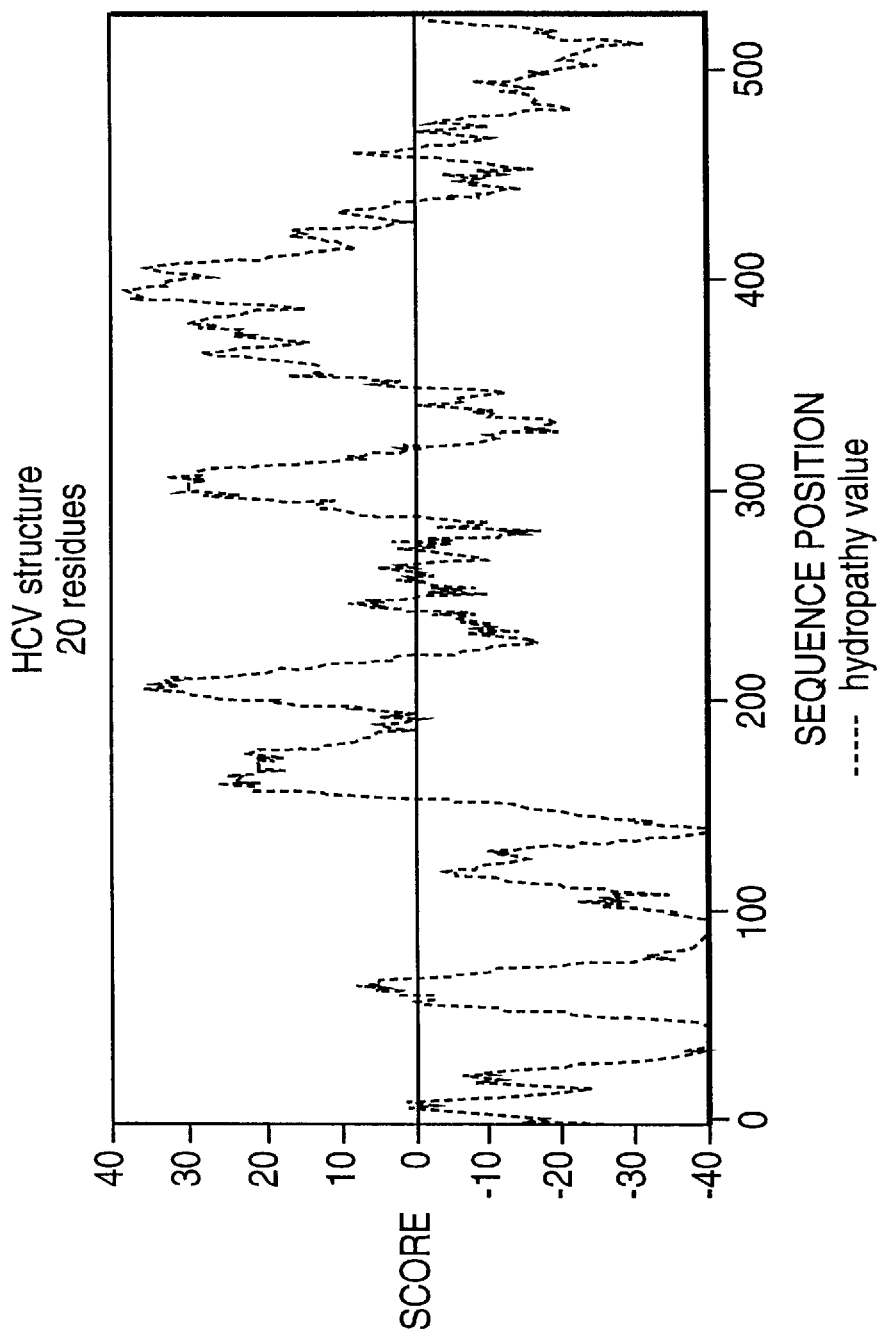
FIG. 2 is a graph showing the results obtained by calculating the "Hydropathy Value" in Example 1 with respect to the core region of HCV.
Figure 3:
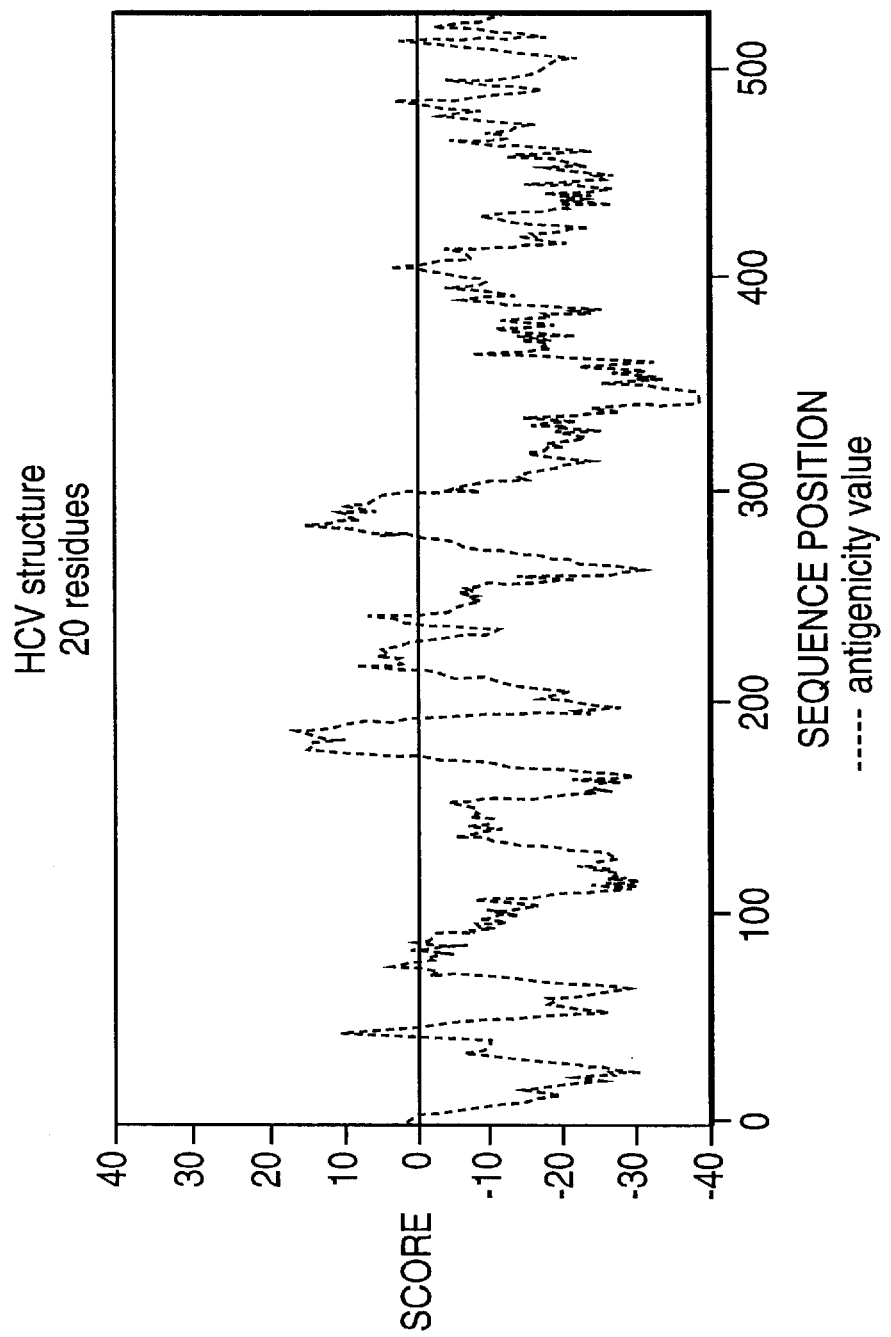
FIG. 3 is a graph showing the results obtained by calculating the "Antigenicity Value" in Example 1 with respect to the core region of HCV.
Figure 4:
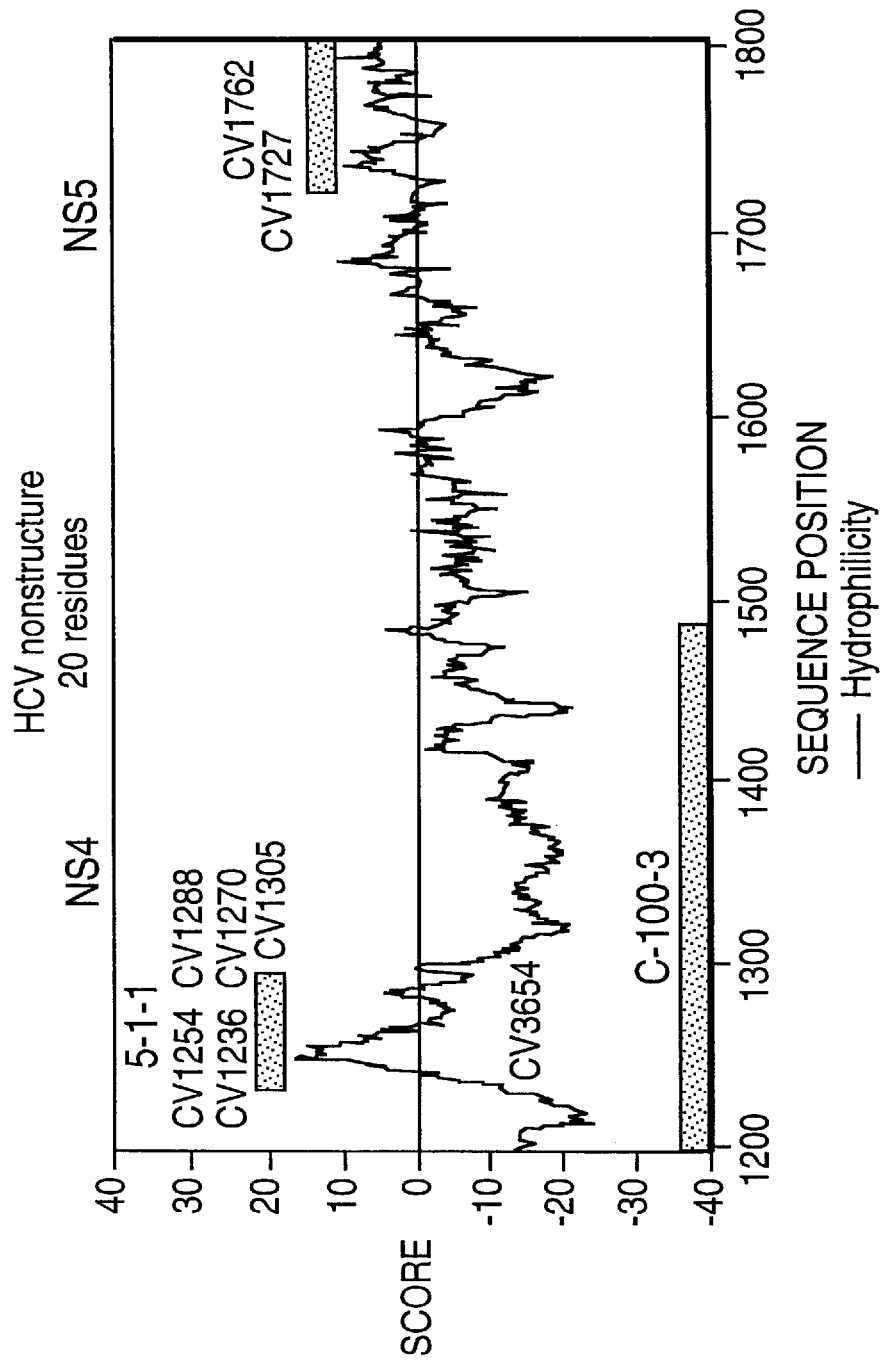
FIG. 4 is a graph showing the results obtained by calculating the "Hydrophilicity Value" in Example 1 with respect to the NS-4 region of HCV.
Figure 5:
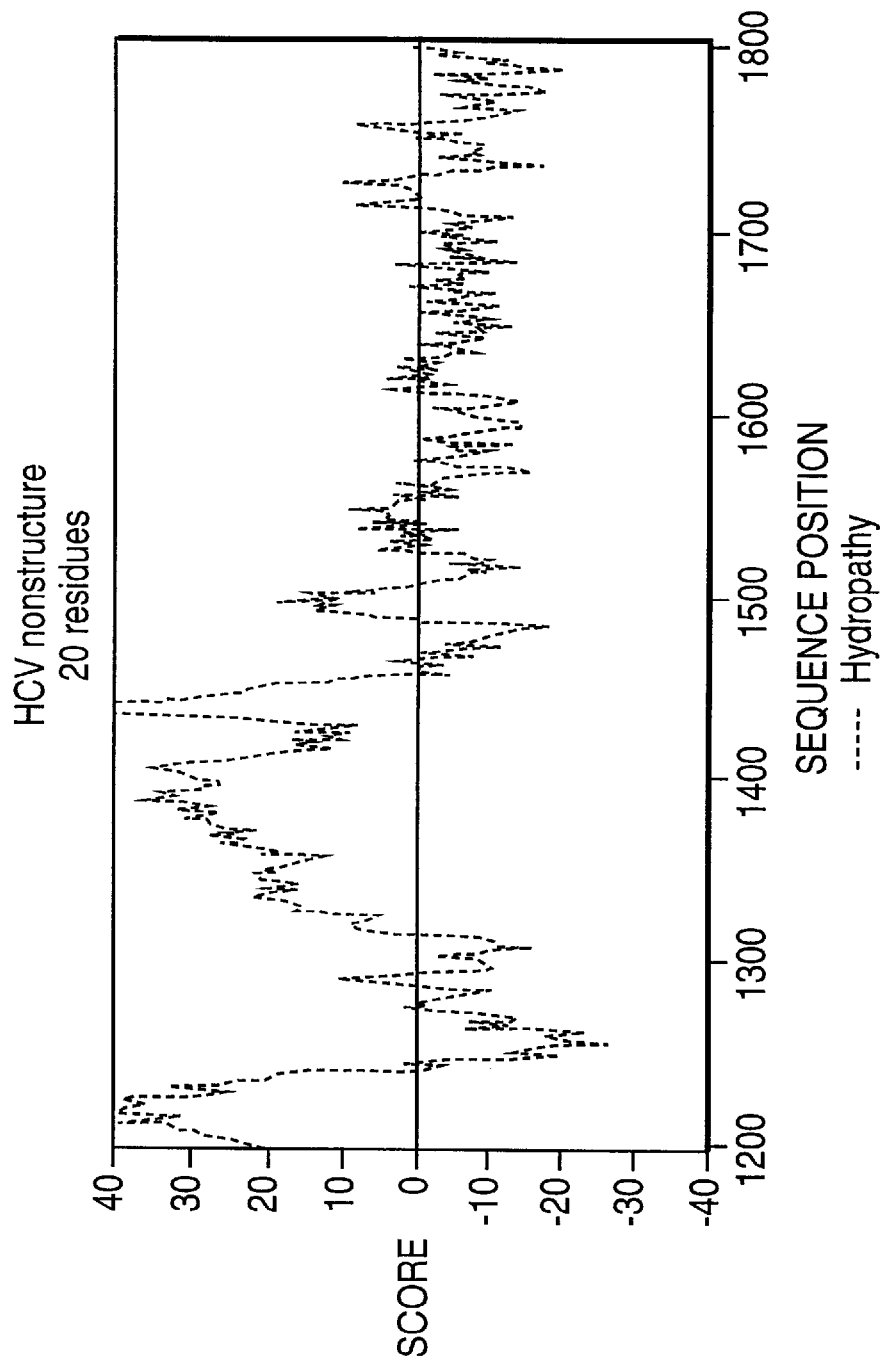
FIG. 5 is a graph showing the results obtained by calculating the "Hydropathy Value" in Example 1 with respect to the NS-4 region of HCV.
Figure 6:
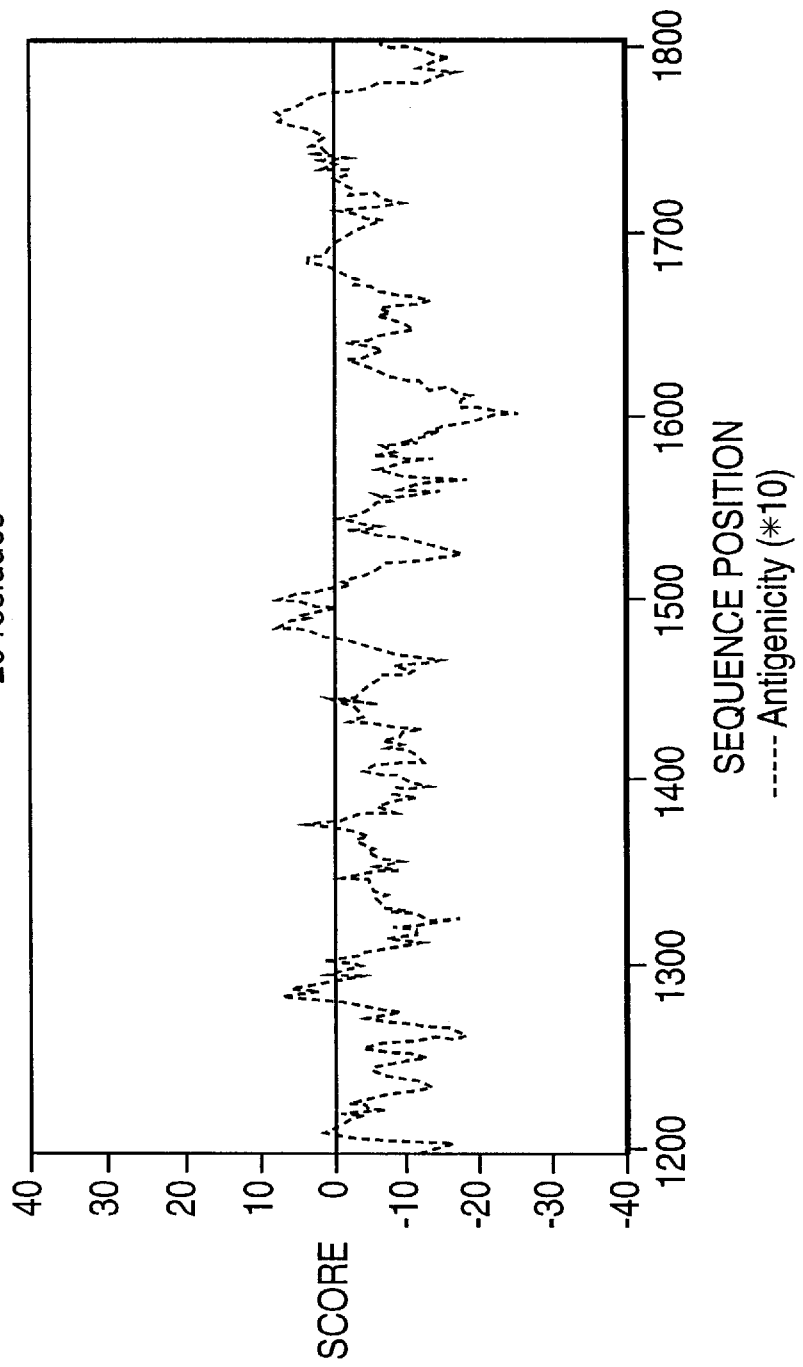
FIG. 6 is a graph showing the results obtained by calculating the "Antigenicity Value" in Example 1 with respect to the NS-4 region of HCV.
Figure 7:
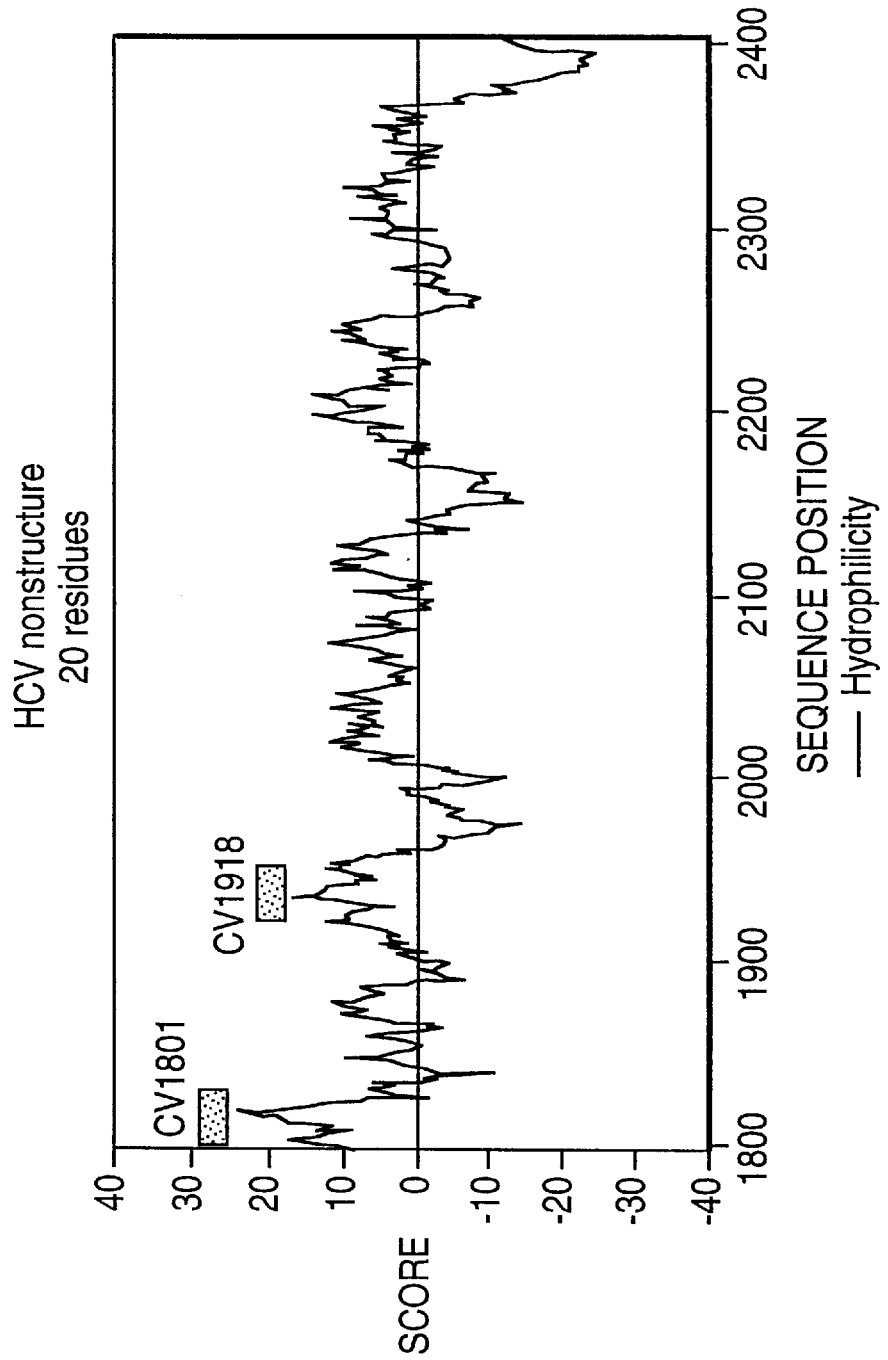
FIG. 7 is a graph showing the results obtained by calculating the "Hydrophilicity Value" in Example 1 with respect to the NS-5 region of HCV.
Figure 8:
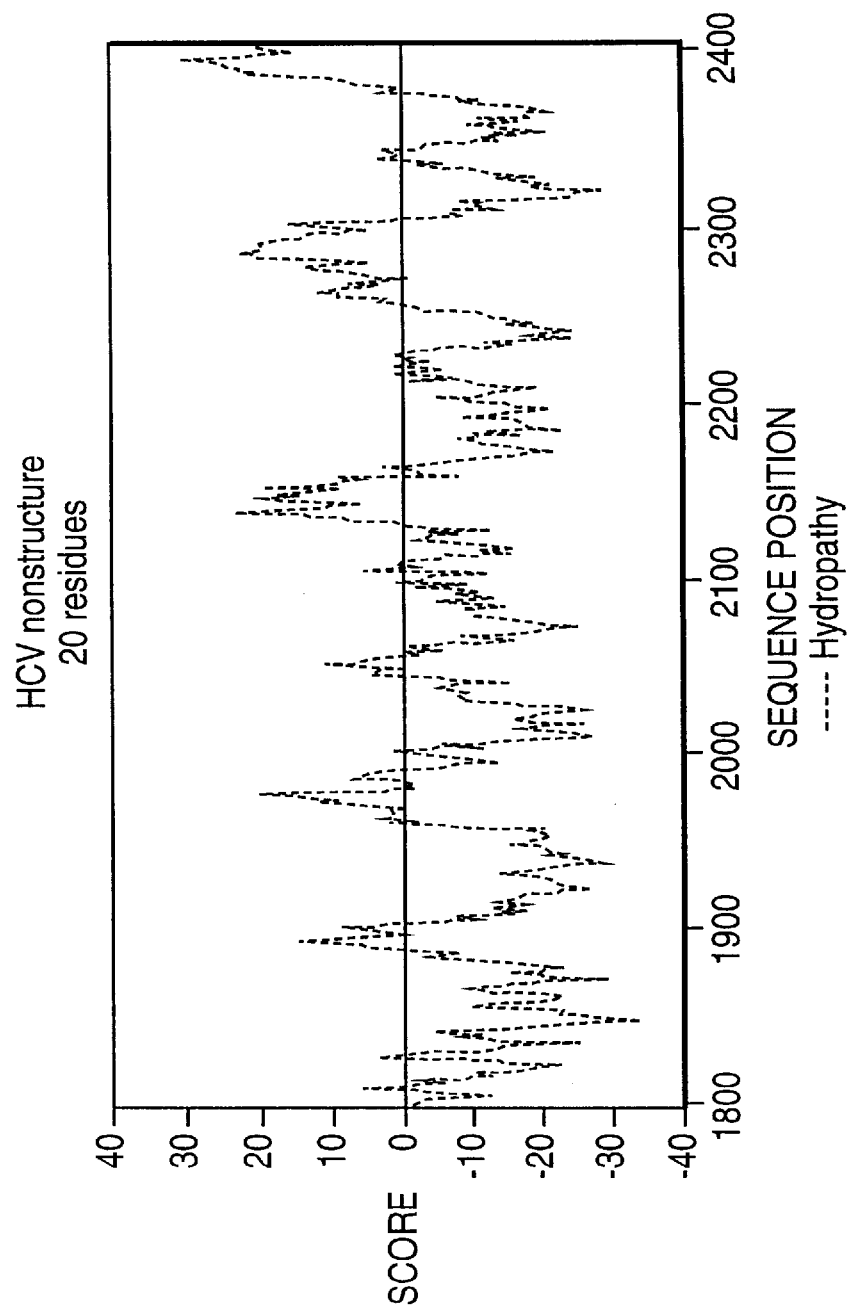
FIG. 8 is a graph showing the results obtained by calculating the "Hydropathy Value" in Example 1 with respect to the NS-5 region of HCV.
Figure 9:
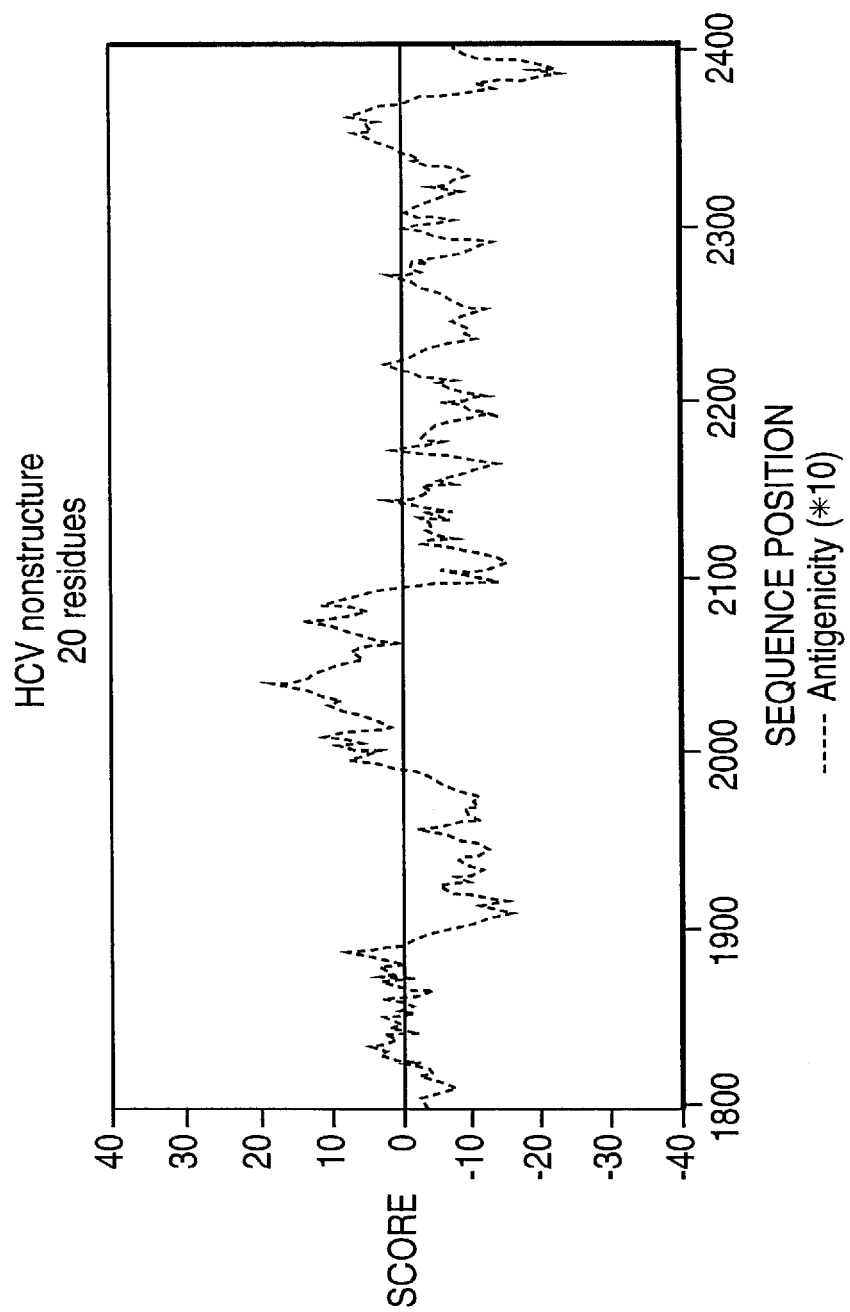
FIG. 9 is a graph showing the results obtained by calculating the "Antigenicity Value" in Example 1 with respect to the NS-5 region of HCV.

At this time, it was also possible to calculate the Hydropathy Value as described in Jack K., Mol. Biol. 157, 105 (1982); and the Antigenicity Value as described in Alan MS., Science, 227, 429 (1985) in a similar same manner as in the calculation of the above Hydrophilicity Value. The results of the calculation using the above Hydrophilicity Value are shown in graphs of FIGS. 1–3 (core region); FIGS. 4–6 (NS-4 region); and FIGS. 7–9 (NS-5 region). These graphs also show the results of the calculation using the above Hydropathy Value and Antigenicity Value, in combination.

Based on the results obtained by using FIGS. 1–9, regions capable of being an antigen of hepatitis C were extracted. Further, among the thus determined regions, regions having a common amino acid sequence with respect to the genotype-I and -II, and regions having a common amino acid sequence with respect to the genotype-III and -IV were determined. As a result of such evaluation, there were discovered the following ckk-n5 and ckk-n6 as antigenic amino acid sequences for the NS-5 region satisfying such conditions.

Leu-Ser-Gly-Arg-Pro-Ala-Ile-Val-Pro-Asp-Arg-Glu-Val-Leu-Tyr-Gln-Glu-Phe-Asp-Glu . . . (ckk-n5)(SEQ ID NO: 1)

Val-Asn-Gln-Arg-Ala-Val-Val-Ala-Pro-Asp-Lys-Glu-Val-Leu-Tyr-Glu-Ala-Phe-Asp-Glu . . . (ckk-n6)(SEQ ID NO: 2)

In the same manner as described above, the following antigenic amino acid sequences of ckk-n3 and ckk-n4 were discovered for the NS-5 region.

Cys-Thr-Thr-His-His-Val-Ser-Pro-Asp-Ala-Asp-Leu-Ile-Glu-Ala-Asn-Leu-Leu-Trp-Arg . . . (ckk-n3)(SEQ ID NO: 3)

Cys-Thr-Thr-His-Gly-Lys-Ala-Tyr-Asp-Val-Asp-Met-Val-Asp-Ala-Asn-Leu-Phe-Met-Gly . . . (ckkn4)(SEQ ID NO: 4)

In the same manner as described above, the following antigenic amino acid sequences of ckk-n1 and ckk-n2 were discovered for the NS-4 region.

Gln-Glu-Phe-Asp-Glu-Met-Glu-Glu-Cys-Ala-Ser-His-Leu-Pro-Tyr-Ile-Glu-Gln-Gly-Met . . . (ckk-n1)(SEQ ID NO: 5)

Glu-Ala-Phe-Asp-Glu-Met-Glu-Glu-Cys-Ala-Ser-Arg-Ala-Ala-Leu-Ile-Glu-Glu-Gly-Gln . . . (ckk-n2)(SEQ ID NO: 6)

In the same manner as described above, the following antigenic amino acid sequences of ckk-c1 and ckk-c2 were discovered for the core region.

Gly-Arg-Arg-Gln-Pro-Ile-Pro-Lys-Ala-Arg-Arg-Pro-Glu-Gly-Arg-Thr-Trp-Ala-Gln-Pro . . . (ckk-c1)(SEQ ID NO: 11)

Gly-Arg-Arg-Gln-Pro-Ile-Pro-Lys-Asp-Arg-Arg-Ser-Thr-Gly-Lys-Ser-Trp-Gly-Lys-Pro . . . (ckk-c2)(SEQ ID NO: 12)

EXAMPLE 2
(Preparation of antigen of hepatitis C)

The above-mentioned HCV antigenic peptides (ckk-n5) and (ckk-n6) were synthesized in the following manner. The peptides were synthesized by means of an automatic peptide synthesizing apparatus of "430A" Peptide Synthesizer mfd. by Applied Biosystems, by use of symmetric anhydride of t-Boc amino acid as a reagent. The resultant synthesized peptide was dissolved in anisole dimethyl sulfide para-thio cresol, and thereafter, was subjected to a reaction at 0°–5° C. for one hour in the presence of hydrofluoric acid, thereby to remove the protecting group (with reference to S. Sakakibara, Bull. Chem. Soc. Jpn., 40, 2164, (1967)).

The resultant crude crystals obtained by the removal of the protecting group was dissolved in 2N-acetic acid, and then extracted by use of ether, and the extract was freeze-dried. The freeze-dried product was purified by means of an HPLC (high-performance liquid chromatography).

This HPLC purification was conducted by using a column (SISEIDO Capsule-Pack C-18 SG120, diameter: 46 mm, length: 250 mm) in a manner such that a gradient was applied to the mobile phase at a flow rate of 12 ml/min by use of a solution comprising 0.1% of trifluoroacetic acid (TFA) and 5% of acetonitrile ($CH_3CN$) in pure water; and a solution comprising 0.1% of TFA and 50% of acetonitrile ($CH_3CN$) in pure water.

Figure 10:
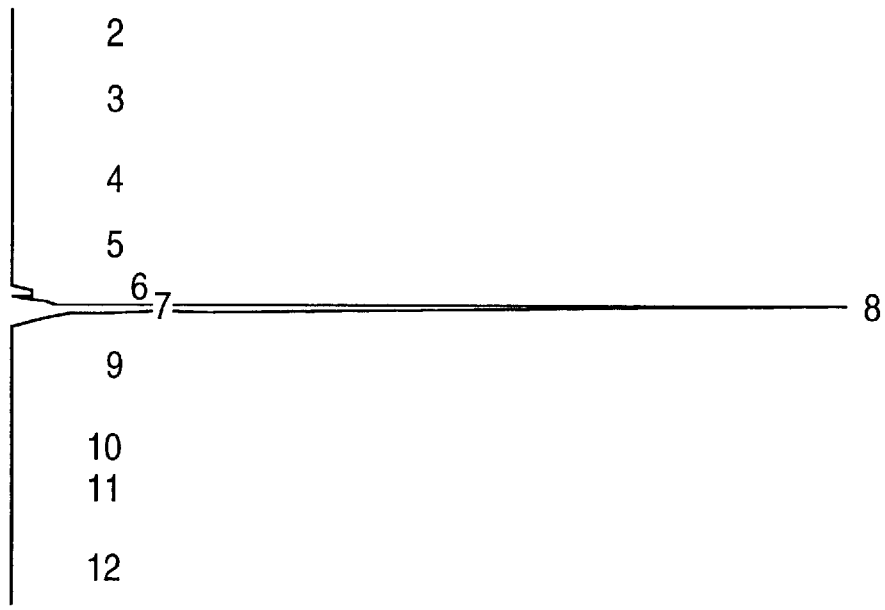
FIG. 10 is a chromatogram showing the results of HPLC analysis of an antigenic peptide compound (1) (ckk-n5) obtained in Example 2.

The chromatogram obtained at this time is shown in FIG. 10. The main peak shown in FIG. 10 corresponds to a synthesized antigenic peptide ckk-n5 of this Example.

Figure 11:
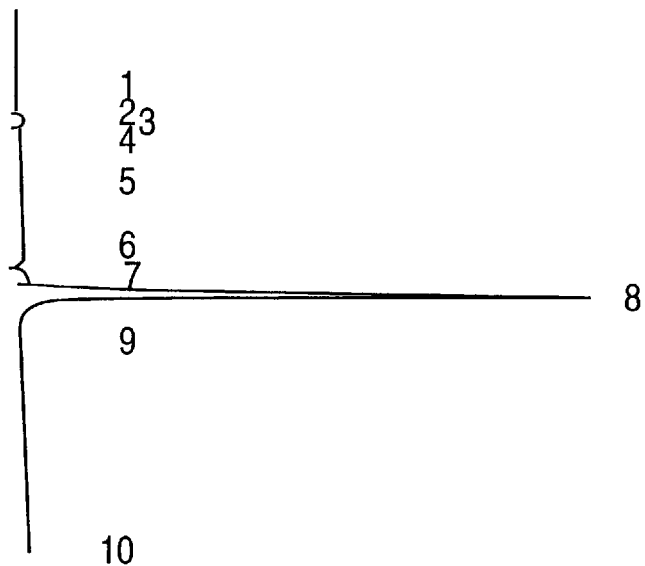
FIG. 11 is a chromatogram showing the results of HPLC analysis of an antigenic peptide compound (2) (ckk-n6) obtained in Example 2.

In the same manner as described above, another synthesized antigenic peptide ckk-n6 was purified by use of HPLC. The chromatogram obtained at this time is shown in FIG. 11. The main peak shown in FIG. 11 corresponds to a synthesized antigenic peptide ckk-n6 of this Example.

In the same manner as described above, the above-mentioned six kinds of synthesized antigenic peptides ckk-n3, ckk-n4, ckk-n1, ckk-n2, ckk-c1 and ckk-c2 were synthesized.

Figure 12:
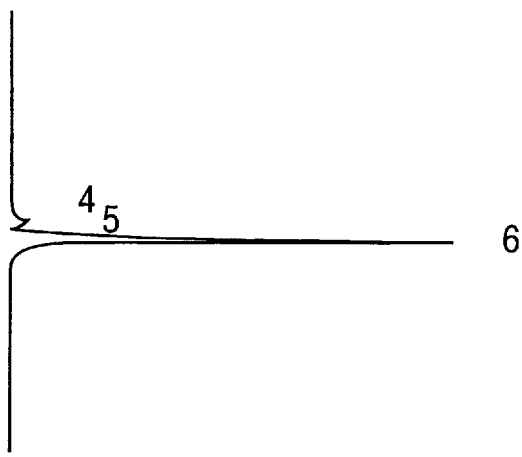
FIG. 12 is a chromatogram showing the results of HPLC analysis of an antigenic peptide compound (3) (ckk-n3) obtained in Example 2.
Figure 13:
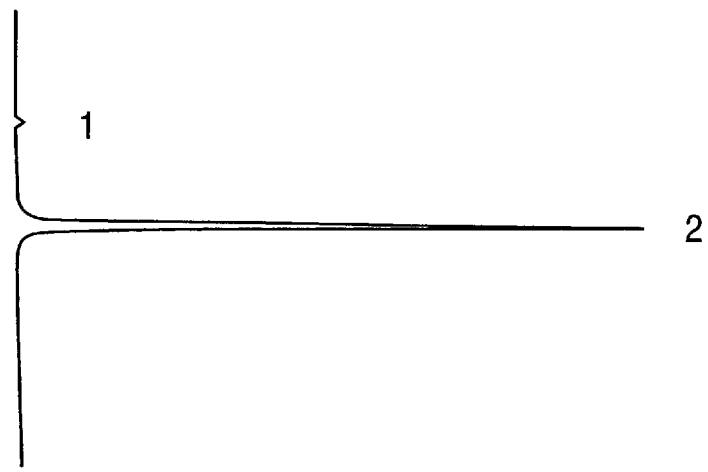
FIG. 13 is a chromatogram showing the results of HPLC analysis of an antigenic peptide compound (4) (ckk-n4) obtained in Example 2.
Figure 14:
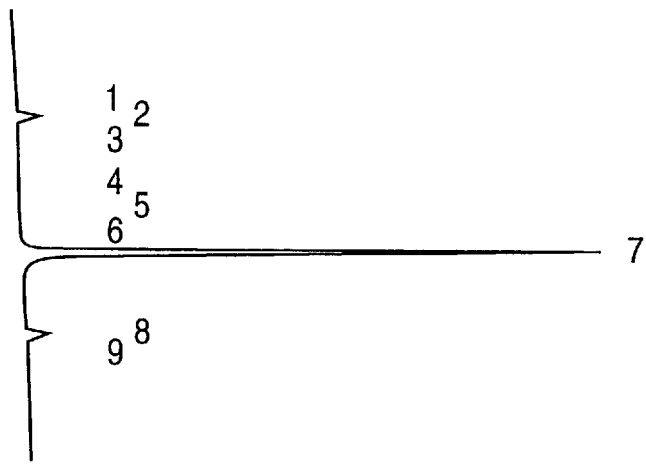
FIG. 14 is a chromatogram showing the results of HPLC analysis of an antigenic peptide compound (5) (ckk-n1) obtained in Example 2.
Figure 15:
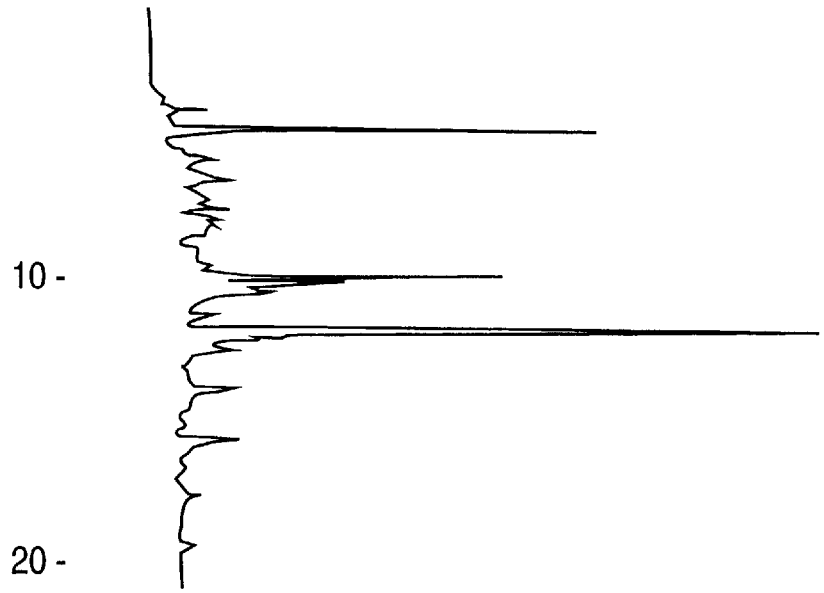
FIG. 15 is a chromatogram showing the results of HPLC analysis of an antigenic peptide compound (6) (ckk-n2) obtained in Example 2.
Figure 16:
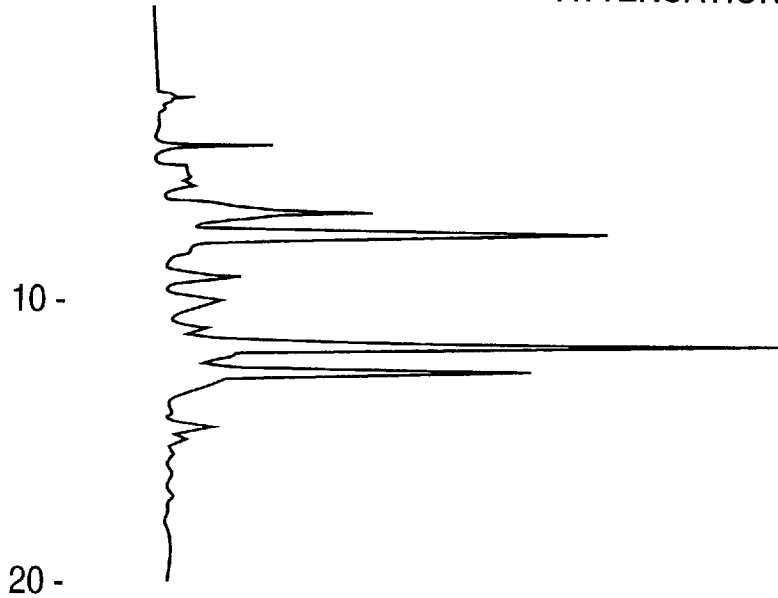
FIG. 16 is a chromatogram showing the results of HPLC analysis of an antigenic peptide compound (7) (ckk-c1) obtained in Example 2.
Figure 17:
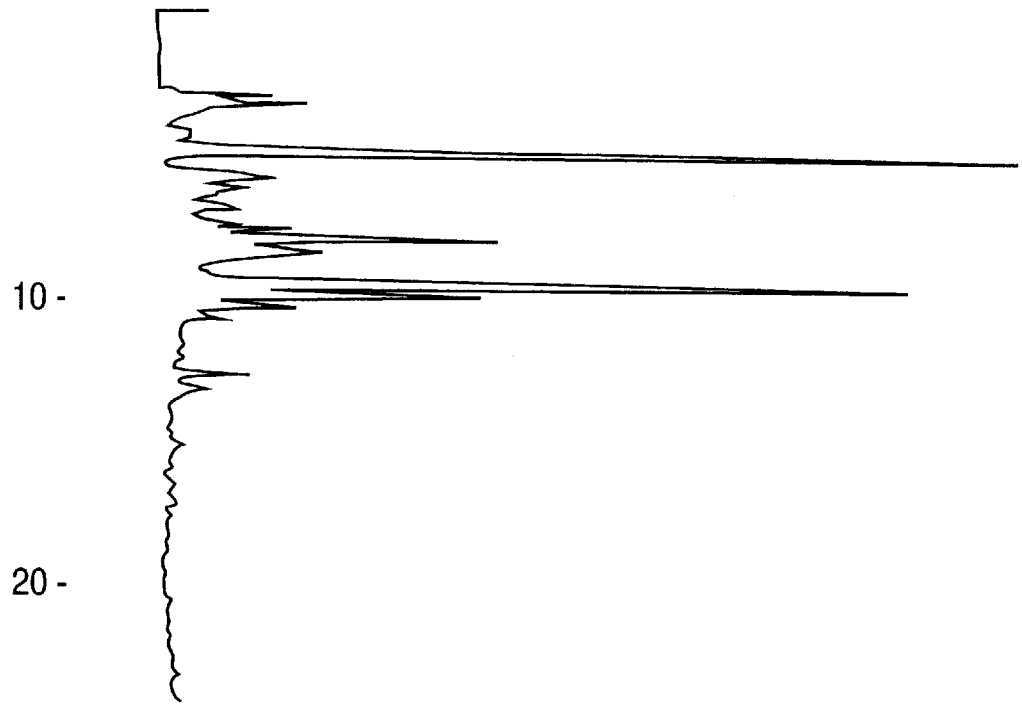
FIG. 17 is a chromatogram showing the results of HPLC analysis of an antigenic peptide compound (8) (ckk-c2) obtained in Example 2.

The HPLC chromatograms obtained at the time of these purifications are respectively shown in FIG. 12 (ckk-n3), FIG. 13 (ckk-n4), FIG. 14 (ckk-n1), FIG. 15 (ckk-n2), FIG. 16 (ckk-c1) and FIG. 17 (ckk-c2).

In the same manner as described above, the following two kinds of synthesized antigenic peptides ckk-n1(40) and ckk-n2(40) were synthesized.

Ile-Ile-Leu-Ser-Gly-Arg-Pro-Ala-Ile-Val-Pro-Asp-Arg-Glu-Leu-Leu-Tyr-Gln-Glu-Phe-Asp-Glu-Met-Glu-Glu-Cys-Ala-Ser-His-Leu-Pro-Tyr-Ile-Glu-Gln-Gly-Met-Gln-Leu-Ala . . . (SEQ ID NO: 9) (ckk-n1(40))

Leu-His-Val-Asn-Gln-Arg-Ala-Val-Val-Ala-Pro-Asp-Lys-Glu-Val-Leu-Tyr-Glu-Ala-Phe-Asp-Glu-Met-Glu-Glu-Cys-Ala-Ser-Arg-Ala-Ala-Leu-Ile-Glu-Glu-Gly-Gln-Arg-Ile-Ala . . . (SEQ ID NO: 10) (ckk-n2(40))

Figure 18:
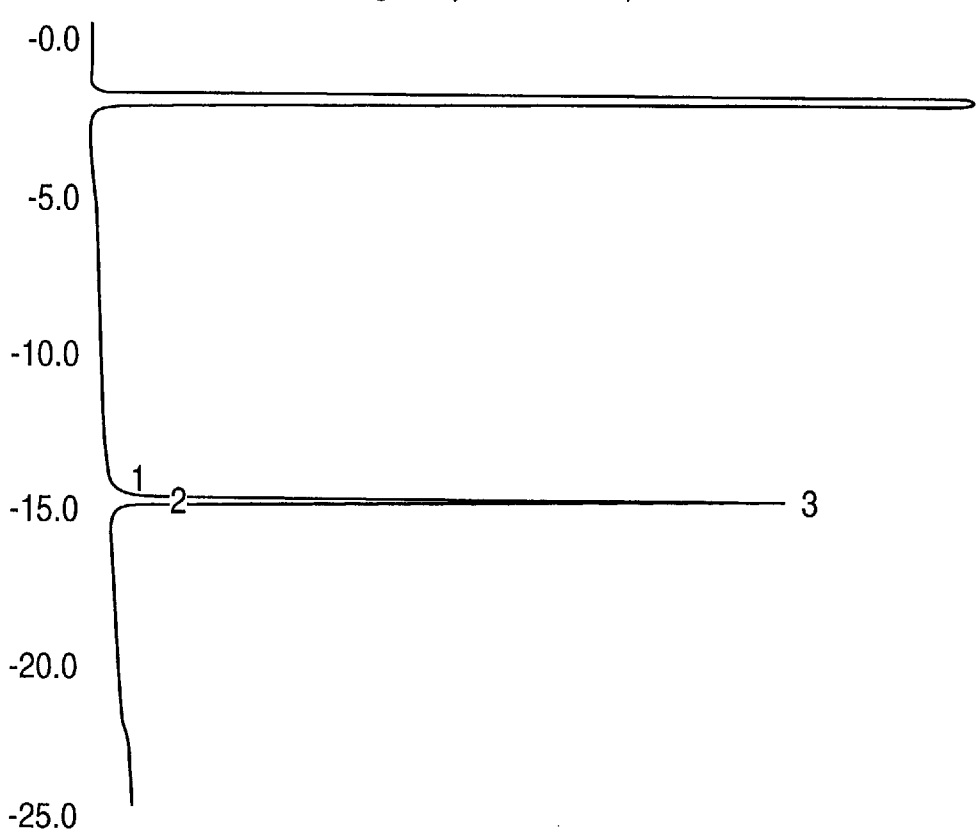
FIG. 18 is a chromatogram showing the results of HPLC analysis of an antigenic peptide compound (9) (ckk-n1 (40)) obtained in Example 2.
Figure 19:
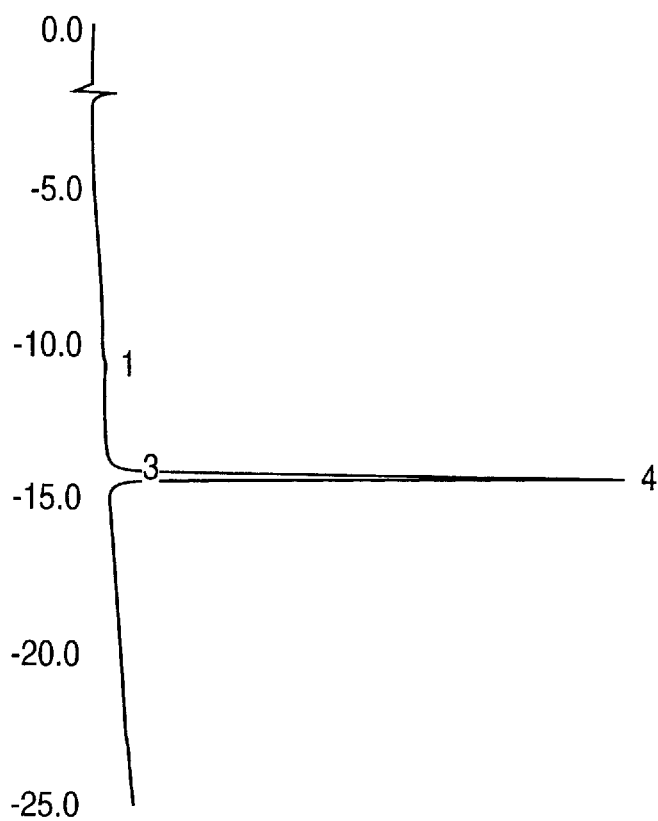
FIG. 19 is a chromatogram showing the results of HPLC analysis of an antigenic peptide compound (10) (ckk-n2(40)) obtained in Example 2.

The HPLC chromatograms obtained at the time of the purification of the above products are respectively shown in FIG. 18 (ckk-n1(40)) and FIG. 19 (ckk-n2(40)).

EXAMPLE 3
(Preparation of plate for ELISA)

The antigenic peptide ckk-n5 obtained in Example 2 was dissolved in 0.15M NaCl-0.10M $Na_2HPO_4$—$NaH_2PO_4.2H_2O$ buffer (PBS), pH=7.0 so as to provide a concentration of 0.04 g/ml. The resultant peptide solution was poured into wells of 96-well micro-plate (trade name: ELISA PLATE 68667, mfd. by NUNC Co.) so that 100 μl of the solution was poured into each of the wells. Then, the micro-plate was left standing at 37° C. for 60 minutes, thereby to solid phase-fix the above antigenic peptide to the micro-plate.

An excess amount of the above peptide solution was removed, and thereafter, the micro-plate was washed three times with 0.01M PBS (pH=7.0). After the washing solution was removed, a solution of gelatine in 0.01M PBS (pH=7.0) having a concentration of 0.1% was poured into the wells so that 300 μl of the solution was poured into each of the wells, and then the micro-plate was left standing at 37° C. for 60 minutes, thereby to coat the micro-plate with the gelatine. After an excess of the above gelatine solution was removed, the micro-plate was washed three times with 0.01M PBS (pH=7.0) containing Tween-20 at a concentration of 0.05%.

The resultant plate coated with the gelatine was dried at 25° C. for six hours, and thereafter, was stored at 4° C. until the plate was used for analyzing specimens.

EXAMPLE 4
(Analysis of specimens)

Specimens (about 100 kinds) were preliminarily subjected to the HCV genotype determination using a PCR method as described in the above-mentioned paper (Okamoto H., KAN TAN SUI, 24, 7–14 (1992)) in Hachioji Laboratory of SRL, Inc., thereby to determine the HCV genotypes thereof.

By use of the above specimens, the HCV genotypes of which had been determined in this manner by using the PCR, the specificity of the antigenic peptide prepared in Example 2 was confirmed in the following manner. This investigation was carried out according to the following procedure by using the micro-plate prepared in Example 3 to which the antigenic peptide had been fixed.

Each of the above specimens was diluted with 0.01M PBS (pH=7.0) containing 0.01% of BSA and 0.05% of Tween-20 so that the resultant volume after the dilution was 50 times the volume of the original specimen. The thus diluted specimen was poured into each of the micro-plate wells in an amount of 100 μl per one well, and then was allowed to react with the above antigenic peptide at 37° C. for 60 minutes (reaction between antigenic peptide—HCV antibody).

After the reaction, the micro-plate was washed five times with 0.01M PBS (pH=7.0) containing 0.05% of Tween-20, and the washing liquid was removed. Thereafter, a peroxidase-labeled anti-human IgG antibody having a concentration of 0.1 μg/20 ml (mfd. by KPL Co.) was added to each of the wells in an amount of 100 μl per one well, and was allowed to cause a reaction at 37° C. for 60 minutes (reaction between HCV antibody—POD-labeled anti-human IgG antibody).

After the reaction, the micro-plate was washed five times with 0.01M PBS (pH=7.0) containing 0.05% of Tween-20, and the washing liquid was removed. Thereafter, 100 μl of 0.023% of hydrogen peroxide, and 100 μl of 0.1M citric acid—Na$_2$HPO$_4$ buffer containing 0.005% of o-phenylene diamine (OPD) were poured into each of the wells, and was allowed to cause a reaction at 37° C. for 30 minutes (reaction for measuring the activity of peroxidase). After the reaction, 50 μl of 5N-sulfuric acid wad added to each of the wells to stop the reaction, the absorbance (ABS or OD) at a wavelength of 491 nm was measured by means of a spectrophotometer (trade name: Plate Reader NJ-2001, mfd. by Nihon Inter-Med Co.).

EXAMPLE 5
(Measurement of specimen using antigenic peptide ckk-n2)

A micro-plate to which an antigenic peptide ckk-n6 had been solid-phase fixed was prepared in the same manner as in Example 3 except for using the antigenic peptide ckk-n6 obtained in Example 2 instead of the antigenic peptide ckk-n5 used in Example 3. Specimens (about 78 kinds), the HCV genotypes of which had preliminarily been determined, were analyzed in the same manner as in Example 4 except for using the thus obtained micro-plate.

The results obtained in the above Examples 4 and 5 are inclusively shown in FIG. 30 (Table 7).

In the above Table 7, the first column corresponds to the identification numbers of the specimens, the second column corresponds to the absorbances (OD values) of specimens in a case where the antigenic peptide ckk-n5 (NS-4L2-1) was used, the third column corresponds to the absorbances of specimens in a case where the antigenic peptide ckk-n6 (NS-4L2-2) was used, the fourth column corresponds to the results (genotypes) of the preliminary determination using the PCR method, and the fifth column corresponds to the results of the determination (serotypes) obtained by the method according to the present invention.

In the serotype determination obtained by the method according to the present invention, the absorbance (ckk-n5) in the first column and the absorbance (ckk-n6) in the second column were compared with each other. When one of the above absorbance values was 1.5 times or more the other of the above absorbance values, the serotype was judged to be a serotype corresponding to the higher one (i.e., when the higher one is ckk-n5 side, it was judged to be serotype-1; and when the higher one is ckk-n6 side, it was judged to be serotype-2).

The results obtained in Examples 4 and 5 were summarized, and were compared with the results of the genotype determination. As a result, the following relationships were obtained (with reference to Hepatology, 16(4), 886, 1992).

<Relationships between serotype and genotype>
Genotype determination serotype determination

| (PCR) | (NS-4) |
|---|---|
| I | Group I |
| II | Group I |
| III | Group II |
| IV | Group II |
| V | — |

(In the above table, "genotype V" also includes such cases, the genotype determinations of which were impossible, or indistinguishable (inclusive of "mixed types") by use of the PCR method.)

EXAMPLE 6
(Measurement of specimens using antigenic peptides ckk-n3 and ckk-n4)

A micro-plate to which an antigenic peptide had been solid-phase fixed was prepared in the same manner as in Example 3 except for using the antigenic peptide ckk-n3 or ckk-n4 corresponding to the NS-5 region obtained in Example 2, respectively, instead of the antigenic peptide ckk-n1 used in Example 3. Specimens (48 kinds), the HCV genotypes of which had preliminarily been determined were analyzed in the same manner as in Example 4 except for using the thus obtained micro-plate.

The results obtained in this Example are inclusively shown in FIG. 31 (Table 8).

In the serotype determination obtained by the method of this Example, in the same manner as in the above Table 7, the absorbance (ckk-n3; NS5L2-1) in the first column and the absorbance (ckk-n4; NS5L2-2) in the second column were compared with each other. When one of the above absorbance values was 1.5 times or more the other of the above absorbance values, the serotype was judged to be a serotype corresponding to the higher one (i.e., when the higher one is ckk-n3 side, it was judged to be serotype-1; and when the higher one is ckk-n4 side, it was judged to be serotype-2).

The results obtained in this Example were summarized, and were compared with the results of the genotype determination. As a result, the following relationships were obtained, similarly as in Examples 4 and 5.
<Relationships between serotype and genotype>
Genotype determination serotype determination

| (PCR) | (NS-5) |
|---|---|
| I | Group I |
| II | Group I |
| III | Group II |
| IV | Group II |
| V | — |

EXAMPLE 7

(Measurement of specimens using antigenic peptides ckk-n1 and ckk-n2)

A micro-plate to which an antigenic peptide had been solid-phase fixed was prepared in the same manner as in Example 3 except for using the antigenic peptide ckk-n1 or ckk-n2 corresponding to the NS-4 region obtained in Example 2, respectively, instead of the antigenic peptide ckk-n5 used in Example 3. Specimens (45 kinds), the HCV genotypes of which had preliminarily been determined, were analyzed in the same manner as in Example 4 except for using the thus obtained micro-plate.

The results obtained in this Example are inclusively shown in FIG. 32 (Table 9).

In the serotype determination obtained by the method of this Example, in the same manner as in the above Table 7, the absorbance (ckk-n1; NS-4L3-1) in the first column and the absorbance (ckk-n2; NS4-L3-2) in the second column were compared with each other. When one of the above absorbance values was 1.5 times or more the other of the above absorbance values, the serotype was judged to be a serotype corresponding to the higher one (i.e., when the higher one is ckk-n1 side, it was judged to be serotype-1; and when the higher one is ckk-n2 side, it was judged to be serotype-2).

The results obtained in this Example were summarized, and were compared with the results of the genotype determination. As a result, the following relationships were obtained, similarly as in Examples 4 and 5.
<Relationships between serotype and genotype>
Genotype determination serotype determination

| (PCR) | (NS-4) |
|---|---|
| I | Group I |
| II | Group I |
| III | Group II |
| IV | Group II |
| V | — |

EXAMPLE 8

(Measurement of specimens using antigenic peptides ckk-c1 and ckk-c2)

A micro-plate to which an antigenic peptide had been solid-phase fixed was prepared in the same manner as in Example 3 except for using the antigenic peptide ckk-c1 or ckk-c2 corresponding to the core region obtained in Example 2, respectively, instead of the antigenic peptide ckk-n5 used in Example 3. Specimens (42 kinds), the HCV genotypes of which had preliminarily been determined, were analyzed in the same manner as in Example 4 except for using the thus obtained micro-plate.

The results obtained in this Example are inclusively shown in FIG. 33 (Table 10).

In the serotype determination obtained by the method of this Example, in the same manner as in the above Table 1, the absorbance (ckk-c1; core-1) in the first column and the absorbance (ckk-c2; core-2) in the second column were compared with each other. When one of the above absorbance values was 1.5 times or more the other of the above absorbance values, the serotype was judged to be a serotype corresponding to the higher one (i.e., when the higher one is ckk-c1 side, it was judged to be serotype-1; and when the higher one is ckk-c2 side, it was judged to be serotype-2).

The results obtained in this Example were summarized, and were compared with the results of the genotype determination. As a result, the following relationships were obtained, similarly as in Examples 4 and 5.
<Relationships between serotype and genotype>
Genotype determination serotype determination

| (PCR) | (core) |
|---|---|
| I | Group I |
| II | Group I |
| III | Group II |
| IV | Group II |
| V | — |

The results of the serotype determination obtained in the above Examples 4–8 are inclusively shown in FIG. 32.

In FIG. 32, the number contained in each of the circles denoting the respective sets represents the number of specimens which were distinguished from each other when the antigenic peptides corresponding to the respective regions were used. The intersection or common region of the respective sets denotes the number of specimens which were commonly distinguished from each other when each of the antigenic peptides corresponding to the respective regions were used.

As described above, the genotype-I and genotype-II showed a good correlation with serotype-I. On the other hand, the genotype-III and genotype-IV showed a good correlation with serotype-II.

In a case where the results of serotype determination obtained by using the antigenic peptides corresponding to the above-mentioned NS-4 region (a combination of NS4-1 and NS4-2), those obtained by using the peptides of the NS-5 region, and those obtained by using the peptides of the core region were combined, it was possible to determine the serotypes of 86% of the specimens, the genotypes of which could be determined, by the method according to the present invention.

EXAMPLE 9

(Measurement of specimens using antigenic peptides ckk-n1(40) and ckk-n2(40))

A micro-plate to which an antigenic peptide had been solid-phase fixed was prepared in the same manner as in Example 3 except for using the antigenic peptide ckk-n1(40) or ckk-n2(40) corresponding to the NS-4 region obtained in Example 2, respectively, instead of the antigenic peptide ckk-n5 used in Example 3. Specimens (100 kinds), the HCV serotypes of which had preliminarily been determined in the same manner as in Example 4 (by use of the antigenic peptide ckk-n5), and in the same manner as in Example 5 (by use of the antigenic peptide ckk-n6), were analyzed in the same manner as in Example 4 except for using the thus obtained micro-plate.

The above 100 kinds of specimens included 83 kinds of specimens of CAH (chronic aggressive hepatitis) patients, and 17 kinds of specimens of CPH (chronic persisting hepatitis) patients.

The results obtained in this Example are inclusively shown in FIG. 34 (Table 11).

In the above Table 11, the results of determination obtained by the method in Examples 4 and 5 (by use of ckk-n5 and ckk-n6 each comprising 20 amino acids as an NS-4 antigenic peptide) are represented by "NS-4 (20)", and the results of determination obtained by the method in this Example (by use of ckk-n1(40) and ckk-n2(40) each comprising 40 amino acids as an NS-4 antigenic peptide) are represented by "NS-4 (40)".

In the above serotype determination by the method in this Example, in the same manner as in the above Table 1, the absorbance obtained by using the ckk-n1(40) and the absorbance obtained by using the ckk-n2(40) were compared with each other. When one of the above absorbance values was 1.5 times or more the other of the above absorbance values, the serotype of the specimen was judged to be a serotype corresponding to the higher one (i.e., when the higher one is ckk-n1(40) side, it was judged to be serotype-1; and when the higher one is ckk-n2(40) side, it was judged to be serotype-2).

As shown in the above Table 11, with respect to the specimens (83 kinds) of CAH, the effectiveness in the determination was improved to 83% (=69÷83) in the case using the NS-4(40), while the effectiveness in the determination was 62% (=52÷83) in the case using the NS-4(20). On the other hand, with respect to the specimens (17 kinds) of CPH, the effectiveness in the determination was improved to 88% (=15÷17) in the case using the NS-4(40), while the effectiveness in the determination was 75% (=13÷17) in the case using the NS-4(20).

EXAMPLE 10

By use of 48 kinds of specimens of CH2A (chronic aggressive hepatitis CAH in which the progressive degree thereof was lower than that of CH2B as described below) patients, 36 kinds of specimens of CH2B (chronic aggressive hepatitis CAH in which the progressive degree thereof was higher than that of CH2A as described above) patients, and 17 kinds of CPH (chronic persisting hepatitis) patients; there were conducted the determination of serotypes (which was conducted in the same manner as in Example 9; the results are shown by "TYPE" in the following Table), the determination of genotypes (which was conducted in the same manner as in Example 4; the results are shown by "SUBTYPE" in the following Table), and the degree of effectiveness of interferon (IFN) (in the following Table, shown by N=not effective, P=partially effective, and C=completely effective).

The results are shown in the following FIG. 35 (Table 12).

In addition, with respect to the same specimens as shown in the above Table 12, there were also conducted serotype determinations using the method using the antigenic peptide of the NS-5 region (the method of Example 6), serotype determinations using the method using the antigenic peptide of the core region (the method of Example 8). The results are shown in FIG. 36 (Table 13) (The results of determination using the above-mentioned ckk-n1(40) and ckk-n2(40) as the "NS-4 region antigenic peptide" in this Example are shown by "NS-4".)

In the above Table 13, the total number obtained by summing the number of CH2A (40 specimens) and the number of CH2B (29 specimens) corresponds to the number of the determinations (69 specimens) using "NS-4(40)" in the above Table 11.

Figure 20:
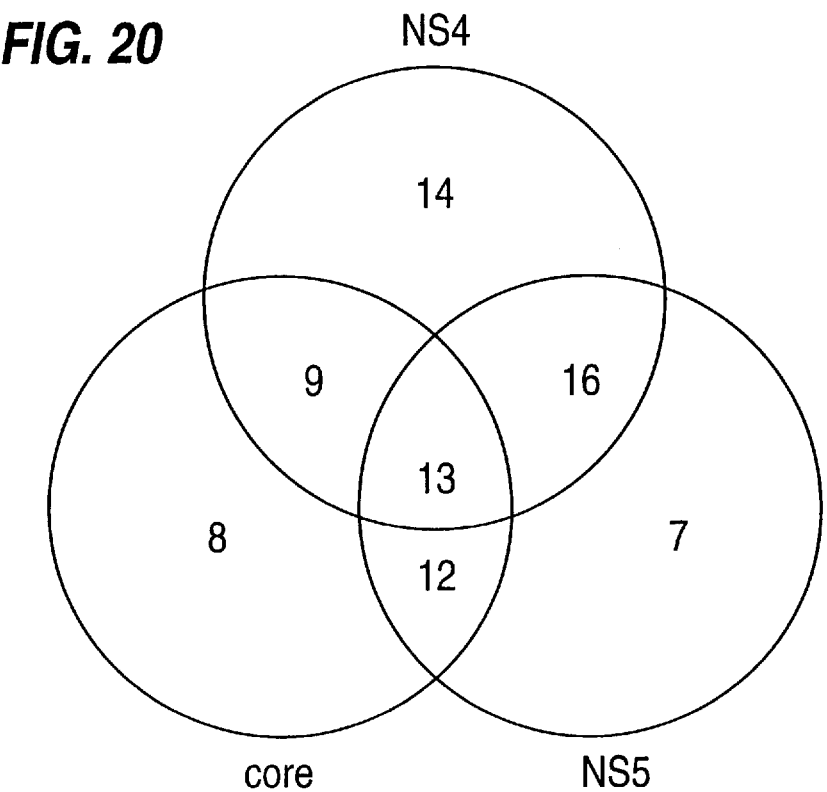
FIG. 20 is a view showing sets obtained by summarizing the results of serotype determination obtained in Examples 4 to 8.
Figure 21:
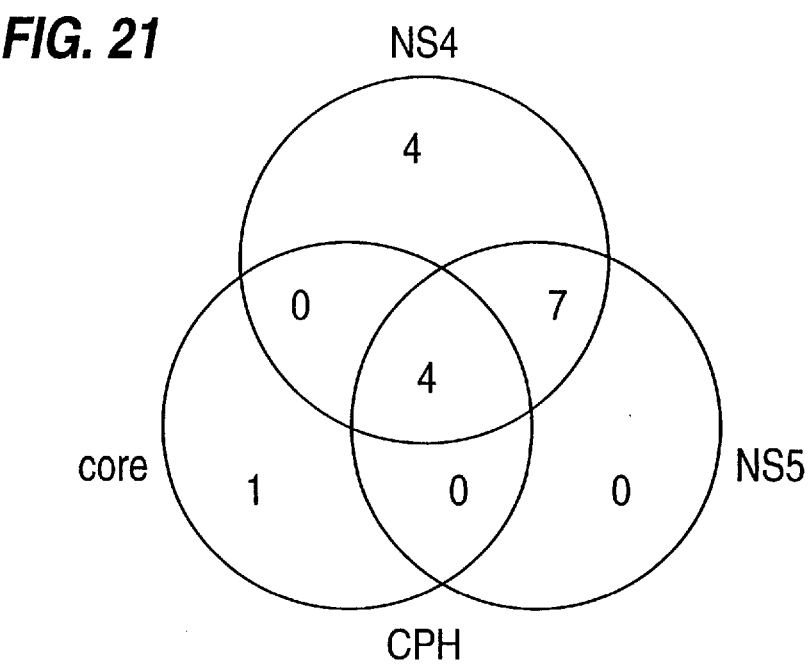
FIG. 21 is a view showing a set obtained by summarizing the results of serotype determination obtained in Examples 9 to 10 with respect to "CPH" specimens.
Figure 22:
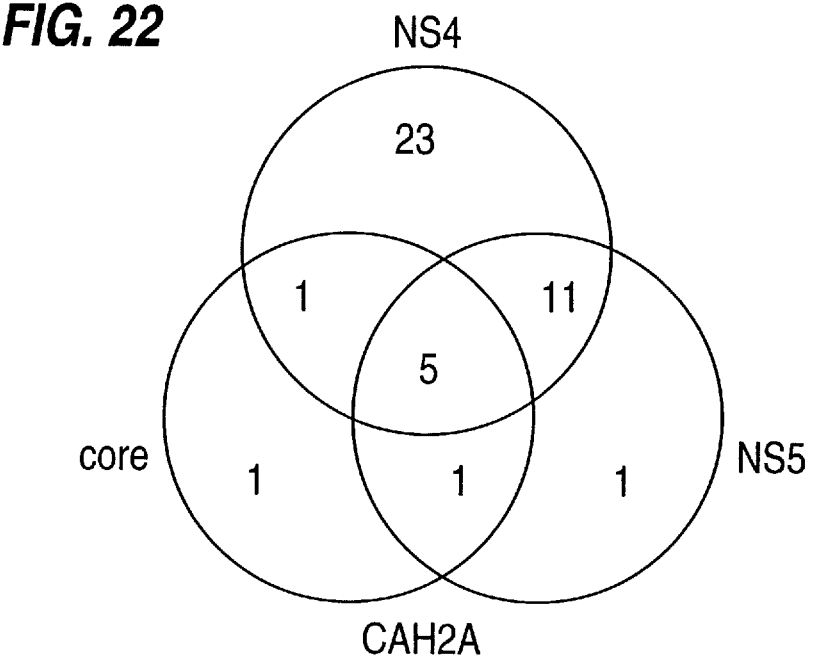
FIG. 22 is a view showing sets obtained by summarizing the results of serotype determination obtained in Examples 9 to 10 with respect to "CPH2A" specimens.
Figure 23:
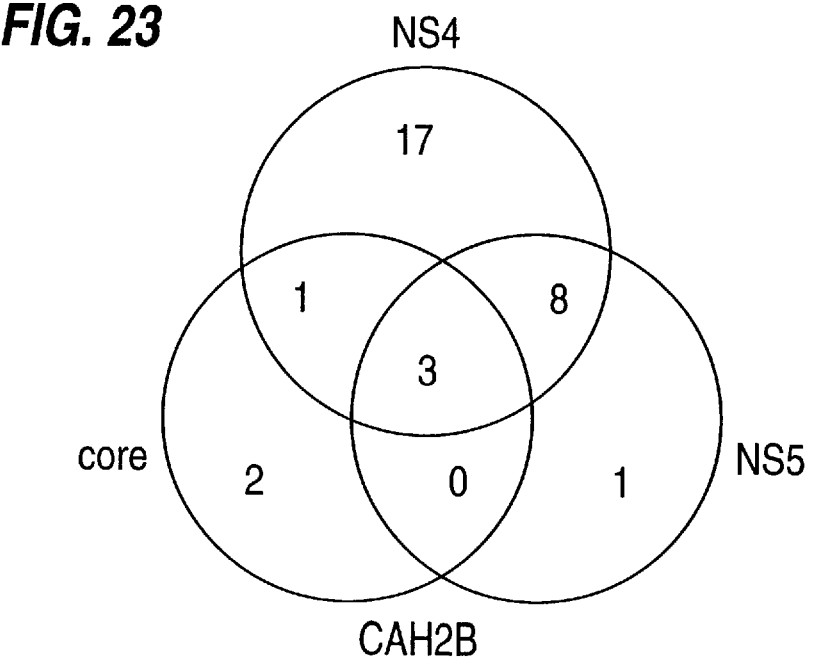
FIG. 23 is a view showing sets obtained by summarizing the results of serotype determination obtained in Examples 9 to 10 with respect to "CPH2B" specimens.

The results of the serotype determination obtained in Examples 9 to 10 are inclusively shown in FIG. 21 (CPH specimens), FIG. 22 (CAH2A specimens), and FIG. 23 (CAH2B specimens), respectively. In FIGS. 19 to 21, the results of determination using the ckk-n1(40) and ckk-n2 (40) as the "NS-4 region antigenic peptide" are represented by "NS-4".

In FIGS. 21 to 23, the number contained in each of the circles denoting the respective sets represents the number of specimens which were distinguished from each other, when the antigenic peptides corresponding to the respective regions were used. The intersection or common region of the respective sets denotes the number of specimens which were commonly distinguished from each other, when the antigenic peptides corresponding to the respective regions were used.

INDUSTRIAL APPLICABILITY

As described hereinabove, the present invention provides an antigenic peptide having an amino acid sequence peculiar to HCV, and a method of measuring an HCV antibody by using such a peptide.

According to the present invention, it is possible to judge the serotype of a specimen simply and accurately, while suppressing a cross reaction or nonspecific reaction. Therefore, according to the present invention, for example, it is possible to preliminarily predict the effect of interferon treatment on the basis of the simple and accurate serotype determination.

Further, it is possible to simply observe the course of the curing or treatment for hepatitis C, on the basis of the measurement of the HCV antibody value according to the present invention.

Further, the present invention provides an antigen for measuring an HCV antibody, which enables HCV antibody determination wherein the genotype-I and genotype-II are distinguished from the genotype-III and genotype-IV; and further a cross reaction or non-specific reaction is suppressed.

Further, the present invention provides a simple method for measuring an HCV antibody which enables HCV antibody determination wherein the genotype-I and genotype-II are distinguished from the genotype-III and genotype-IV.

Further, the present invention provides a method for measuring HCV antibody, which enables HCV antibody determination wherein the genotype-I and genotype-II are distinguished from the genotype-III and genotype-IV; and cross reaction or non-specific reaction is suppressed.

Further, the present invention provides a low-cost method for measuring HCV antibody, which enables HCV antibody determination wherein the genotype-I and genotype-II are distinguished from the genotype-III and genotype-IV.

I claim:

1. An antigenic peptide, of twenty or forty sequential amino acids from an amino acid sequence selected from the group consisting of formulae (1) and (3)–(10):

Leu-Ser-Gly-Arg-Pro-Ala-Ile-Val-Pro-Asp-Arg-Glu-Val-Leu-Tyr-Gln-Glu-Phe-Asp-Glu . . . (1) (ckk-n5, SEQ ID NO:1);

Cys-Thr-Thr-His-His-Val-Ser-Pro-Asp-Ala-Asp-Leu-Ile-Glu-Ala-Asn-Leu-Leu-Trp-Arg . . . (3) (ckk-n3, SEQ ID NO:3);

Cys-Thr-Thr-His-Gly-Lys-Ala-Tyr-Asp-Val-Asp-Met-Val-Asp-Ala-Asn-Leu-Phe-Met-Gly . . . (4) (ckk-n4, SEQ ID NO:4);

Gln-Glu-Phe-Asp-Glu-Met-Glu-Glu-Cys-Ala-Ser-His-Leu-Pro-Tyr-Ile-Glu-Gln-Gly-Met . . . (5) (ckk-n1, SEQ ID NO:5);

Glu-Ala-Phe-Asp-Glu-Met-Glu-Glu-Cys-Ala-Ser-Arg-Ala-Ala-Leu-Ile-Glu-Glu-Gly-Gln . . . (6) (ckk-n2, SEQ ID NO:6);

Gly-Arg-Arg-Gln-Pro-Ile-Pro-Lys-Ala-Arg-Arg-Pro-Glu-Gly-Arg-Thr-Trp-Ala-Gln-Pro . . . (7) (SEQ ID NO:7);

Gly-Arg-Arg-Gln-Pro-Ile-Pro-Lys-Asp-Arg-Arg-Ser-Thr-Gly-Lys-Ser-Trp-Gly-Lys-Pro . . . (8) (SEQ ID NO:8);

Ile-Ile-Leu-Ser-Gly-Arg-Pro-Ala-Ile-Val-Pro-Asp-Arg-Glu-Leu-Leu-Tyr-Gln-Glu-Phe-Asp-Glu-Met-Glu-Glu-Cys-Ala-Ser-His-Leu-Pro-Tyr-Ile-Glu-Gln-Gly-Met-Gln-Leu-Ala . . . (9) (ckk-n1 (40), SEQ ID NO:9); and Leu-His-Val-Asn-Gln-Arg-Ala-Val-Val-Ala-Pro-Asp-Lys-Glu-Val-Leu-Tyr-Glu-Ala-Phe-Asp-Glu-Met-Glu-Glu-Cys-Ala-Ser-Arg-Ala-Ala-Leu-Ile-Glu-Glu-Gly-Gln-Arg-Ile-Ala . . . (10) (ckk-n2(40), SEQ ID NO:10).

2. An antigenic peptide according to claim 1, wherein said amino acid sequence is represented by the following formula (1):

Leu-Ser-Gly-Arg-Pro-Ala-Ile-Val-Pro-Asp-Arg-Glu-Val-Leu-Tyr-Gln-Glu-Phe-Asp-Glu . . . (SEQ ID NO: 1) (ckk-n5).

3. An antigenic peptide according to claim 1, wherein said amino acid sequence is represented by the following formula (3):

Cys-Thr-Thr-His-His-Val-Ser-Pro-Asp-Ala-Asp-Leu-Ile-Glu-Ala-Asn-Leu-Leu-Trp-Arg . . . (SEQ ID NO: 3) (ckk-n3).

4. An antigenic peptide according to claim 1, wherein said amino acid sequence is represented by the following formula (4):

Cys-Thr-Thr-His-Gly-Lys-Ala-Tyr-Asp-Val-Asp-Met-Val-Asp-Ala-Asn-Leu-Phe-Met-Gly . . . (SEQ ID NO: 4) (ckk-n4).

5. An antigenic peptide according to claim 1, wherein said amino acid sequence is represented by the following formula (5):

Gln-Glu-Phe-Asp-Glu-Met-Glu-Glu-Cys-Ala-Ser-His-Leu-Pro-Tyr-Ile-Glu-Gln-Gly-Met . . . (SEQ ID NO: 5) (ckk-n1).

6. An antigenic peptide according to claim 1, wherein said amino acid sequence is represented by the following formula (6):

Glu-Ala-Phe-Asp-Glu-Met-Glu-Glu-Cys-Ala-Ser-Arg-Ala-Ala-Leu-Ile-Glu-Glu-Gly-Gln . . . (SEQ ID NO: 6) (ckk-n2).

7. An antigenic peptide according to claim 1, wherein said amino acid sequence is represented by the following formula (7):

Gly-Arg-Arg-Gln-Pro-Ile-Pro-Lys-Ala-Arg-Arg-Pro-Glu-Gly-Arg-Thr-Trp-Ala-Gln-Pro . . . (SEQ ID NO: 7).

8. An antigenic peptide according to claim 1, wherein said amino acid sequence is represented by the following formula (8):

Gly-Arg-Arg-Gln-Pro-Ile-Pro-Lys-Asp-Arg-Arg-Ser-Thr-Gly-Lys-Ser-Trp-Gly-Lys-Pro . . . (SEQ ID NO: 8).

9. An antigenic peptide according to claim 1, wherein said amino acid sequence is represented by the following formula (9):

Ile-Ile-Leu-Ser-Gly-Arg-Pro-Ala-Ile-Val-Pro-Asp-Arg-Glu-Leu-Leu-Tyr-Gln-Glu-Phe-Asp-Glu-Met-Glu-Glu-Cys-Ala-Ser-His-Leu-Pro-Tyr-Ile-Glu-Gln-Gly-Met-Gln-Leu-Ala . . . (SEQ ID NO: 9) (ckk-n1 (40)).

10. An antigenic peptide according to claim 1, wherein said amino acid sequence is represented by the following formula (10):

Leu-His-Val-Asn-Gln-Arg-Ala-Val-Val-Ala-Pro-Asp-Lys-Glu-Val-Leu-Tyr-Glu-Ala-Phe-Asp-Glu-Met-Glu-Glu-Cys-Ala-Ser-Arg-Ala-Ala-Leu-Ile-Glu-Glu-Gly-Gln-Arg-Ile-Ala . . . (SEQ ID NO: 10) (ckk-n2(40)).

11. An immunoassay for determining hepatitis C virus (HCV) antibodies in a biological sample, comprising;

contacting said sample with an antigenic peptide according to claim 1; and determining the extent of binding of antibodies in said sample to said antigenic peptide.

12. An immunoassay according to claim 11, wherein the extent of binding of an enzyme-labelled ligand is used to determine the extent of binding of said antibodies.

13. An immunoassay according to claim 11, wherein the extent of binding of a radioactive substance-labelled ligand is used to determine the extent of binding of said antibodies.

14. An immunoassay according to claim 11, wherein the extent of binding of a fluorescent substance-labelled ligand is used to determine the extent of binding of said antibodies.

15. An immunoassay according to claim 11, wherein said antigenic peptide is bound to a solid support.

16. An immunoassay according to claim 11, wherein a combination of two or three of said antigenic peptides is used, selected from different groups of peptides, said groups being NS-4-1 or NS-4-40 (peptides 1, 9 and 10, SEQ ID NOS: 1, 9 and 10); NS-4-2 (peptides 5 and 6, SEQ ID NOS:5 and 6); NS-5 (peptides 3 and 4, SEQ ID NOS:3 and 4); and core (peptides 7 and 8, SEQ ID NOS:7 AND 8).

* * * * *

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( x i ) SEQUENCE DESCRIPTION: SEQ ID NO:1:

```
Leu  Ser  Gly  Arg  Pro  Ala  Ile  Val  Pro  Asp  Arg  Glu  Val  Leu  Tyr  Gln
 1              5                        10                       15

Glu  Phe  Asp  Glu
                20
```

( 2 ) INFORMATION FOR SEQ ID NO:2:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( x i ) SEQUENCE DESCRIPTION: SEQ ID NO:2:

```
Val  Asn  Gln  Arg  Ala  Val  Val  Ala  Pro  Asp  Lys  Glu  Val  Leu  Tyr  Glu
 1              5                        10                       15

Ala  Phe  Asp  Glu
                20
```

( 2 ) INFORMATION FOR SEQ ID NO:3:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( x i ) SEQUENCE DESCRIPTION: SEQ ID NO:3:

```
Cys  Thr  Thr  His  His  Val  Ser  Pro  Asp  Ala  Asp  Leu  Ile  Glu  Ala  Asn
 1              5                        10                       15

Leu  Leu  Trp  Arg
                20
```

( 2 ) INFORMATION FOR SEQ ID NO:4:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( x i ) SEQUENCE DESCRIPTION: SEQ ID NO:4:

```
Cys  Thr  Thr  His  Gly  Lys  Ala  Tyr  Asp  Val  Asp  Met  Val  Asp  Ala  Asn
 1              5                        10                       15

Leu  Phe  Met  Gly
                20
```

( 2 ) INFORMATION FOR SEQ ID NO:5:

( i ) SEQUENCE CHARACTERISTICS:
    ( A ) LENGTH: 20 amino acids (B) TYPE: amino acid
(C) STRANDEDNESS: single
(D) TOPOLOGY: linear (xi) SEQUENCE DESCRIPTION: SEQ ID NO:5:

Gln Glu Phe Asp Glu Met Glu Glu Cys Ala Ser His Leu Pro Tyr Ile
1               5                   10                  15
Glu Gln Gly Met
        20

(2) INFORMATION FOR SEQ ID NO:6:

(i) SEQUENCE CHARACTERISTICS:
(A) LENGTH: 20 amino acids
(B) TYPE: amino acid
(C) STRANDEDNESS: single
(D) TOPOLOGY: linear (xi) SEQUENCE DESCRIPTION: SEQ ID NO:6:

Glu Ala Phe Asp Glu Met Glu Glu Cys Ala Ser Arg Ala Ala Leu Ile
1               5                   10                  15
Glu Glu Gly Gln
        20

(2) INFORMATION FOR SEQ ID NO:7:

(i) SEQUENCE CHARACTERISTICS:
(A) LENGTH: 20 amino acids
(B) TYPE: amino acid
(C) STRANDEDNESS: single
(D) TOPOLOGY: linear (xi) SEQUENCE DESCRIPTION: SEQ ID NO:7:

Gly Arg Arg Gln Pro Ile Pro Lys Ala Arg Arg Pro Glu Gly Arg Thr
1               5                   10                  15
Trp Ala Gln Pro
        20

(2) INFORMATION FOR SEQ ID NO:8:

(i) SEQUENCE CHARACTERISTICS:
(A) LENGTH: 20 amino acids
(B) TYPE: amino acid
(C) STRANDEDNESS: single
(D) TOPOLOGY: linear (xi) SEQUENCE DESCRIPTION: SEQ ID NO:8:

Gly Arg Arg Gln Pro Ile Pro Lys Asp Arg Arg Ser Thr Gly Lys Ser
1               5                   10                  15
Trp Gly Lys Pro
        20

(2) INFORMATION FOR SEQ ID NO:9:

(i) SEQUENCE CHARACTERISTICS:
(A) LENGTH: 40 amino acids
(B) TYPE: amino acid
(C) STRANDEDNESS: single
(D) TOPOLOGY: linear (xi) SEQUENCE DESCRIPTION: SEQ ID NO:9:

Ile Ile Leu Ser Gly Arg Pro Ala Ile Val Pro Asp Arg Glu Leu Leu
1               5                   10                  15
Tyr Gln Glu Phe Asp Glu Met Glu Glu Cys Ala Ser His Leu Pro Tyr
        20                  25                  30

Ile Glu Gln Gly Met Gln Leu Ala
                35                  40

( 2 ) INFORMATION FOR SEQ ID NO:10:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

Leu His Val Asn Gln Arg Ala Val Val Ala Pro Asp Lys Glu Val Leu
1                   5                           10                          15

Tyr Glu Ala Phe Asp Glu Met Glu Glu Cys Ala Ser Arg Ala Ala Leu
                20                          25                          30

Ile Glu Glu Gly Gln Arg Ile Ala
                35                  40

( 2 ) INFORMATION FOR SEQ ID NO:11:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( x i ) SEQUENCE DESCRIPTION: SEQ ID NO:11:

Gly Arg Arg Gln Pro Ile Pro Lys Ala Arg Arg Pro Glu Gly Arg Thr
1                   5                           10                          15

Trp Ala Gln Pro
                20

( 2 ) INFORMATION FOR SEQ ID NO:12:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

Gly Arg Arg Gln Pro Ile Pro Lys Asp Arg Arg Ser Thr Gly Lys Ser
1                   5                           10                          15

Trp Gly Lys Pro
                20

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:13:

Leu Ser Gly Arg Pro Ala Ile Val Pro Asp
1                   5                           10

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

Arg Glu Leu Leu Tyr Gln Glu Phe Asp Glu
1               5                   10

( 2 ) INFORMATION FOR SEQ ID NO:15:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( x i ) SEQUENCE DESCRIPTION: SEQ ID NO:15:

Ala Ile Val Pro Asp Arg Glu Leu Leu Tyr
1               5                   10

( 2 ) INFORMATION FOR SEQ ID NO:16:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( x i ) SEQUENCE DESCRIPTION: SEQ ID NO:16:

Arg Pro Ala Ile Val Pro Asp Arg Glu Leu Leu Tyr Gln Glu
1               5                   10

( 2 ) INFORMATION FOR SEQ ID NO:17:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( x i ) SEQUENCE DESCRIPTION: SEQ ID NO:17:

Pro Ala Ile Val Pro Asp Arg Glu Leu Leu Tyr Gln
1               5                   10

( 2 ) INFORMATION FOR SEQ ID NO:18:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( x i ) SEQUENCE DESCRIPTION: SEQ ID NO:18:

Val Asn Gln Arg Ala Val Val Ala Pro Asp
1               5                   10

( 2 ) INFORMATION FOR SEQ ID NO:19:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( x i ) SEQUENCE DESCRIPTION: SEQ ID NO:19:

Lys Glu Val Leu Tyr Glu Ala Phe Asp Glu
1               5                   10

( 2 ) INFORMATION FOR SEQ ID NO:20:

( i ) SEQUENCE CHARACTERISTICS:
      ( A ) LENGTH: 10 amino acids (B) TYPE: amino acid
(C) STRANDEDNESS: single
(D) TOPOLOGY: linear (xi) SEQUENCE DESCRIPTION: SEQ ID NO:20:

Val Val Ala Pro Asp Lys Glu Val Leu Tyr
1               5                   10

(2) INFORMATION FOR SEQ ID NO:21:

(i) SEQUENCE CHARACTERISTICS:
(A) LENGTH: 14 amino acids
(B) TYPE: amino acid
(C) STRANDEDNESS: single
(D) TOPOLOGY: linear (xi) SEQUENCE DESCRIPTION: SEQ ID NO:21:

Arg Ala Val Val Ala Pro Asp Lys Glu Val Leu Tyr Glu Ala
1               5                   10

(2) INFORMATION FOR SEQ ID NO:22:

(i) SEQUENCE CHARACTERISTICS:
(A) LENGTH: 12 amino acids
(B) TYPE: amino acid
(C) STRANDEDNESS: single
(D) TOPOLOGY: linear (xi) SEQUENCE DESCRIPTION: SEQ ID NO:22:

Ala Val Val Ala Pro Asp Lys Glu Val Leu Tyr Glu
1               5                   10

(2) INFORMATION FOR SEQ ID NO:23:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO:23:

Cys Thr Thr His His Val Ser Pro Asp Ala
1               5                   10

(2) INFORMATION FOR SEQ ID NO:24:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO:24:

Asp Leu Ile Glu Ala Asn Leu Leu Trp Arg
1               5                   10

(2) INFORMATION FOR SEQ ID NO:25:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO:25:

Val Ser Pro Asp Ala Asp Leu Ile Glu Ala
1               5                   10

(2) INFORMATION FOR SEQ ID NO:26:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:26:

```
His His Val Ser Pro Asp Ala Asp Leu Ile Glu Ala Asn Leu
 1               5                   10
```

(2) INFORMATION FOR SEQ ID NO:27:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:27:

```
His Val Ser Pro Asp Ala Asp Leu Ile Glu Ala Asn
 1           5                   10
```

(2) INFORMATION FOR SEQ ID NO:28:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:28:

```
Cys Thr Thr His Gly Lys Ala Tyr Asp Val
 1           5                   10
```

(2) INFORMATION FOR SEQ ID NO:29:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:29:

```
Asp Met Val Asp Ala Asn Leu Phe Met Gly
 1           5                   10
```

(2) INFORMATION FOR SEQ ID NO:30:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:30:

```
Lys Ala Tyr Asp Val Asp Met Val Asp Ala
 1           5                   10
```

(2) INFORMATION FOR SEQ ID NO:31:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:31:

His Gly Lys Ala Tyr Asp Val Asp Met Val Asp Ala Asn Leu
1               5                   10

(2) INFORMATION FOR SEQ ID NO:32:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:32:

Gly Lys Ala Tyr Asp Val Asp Met Val Asp Ala Asn
1               5                   10

(2) INFORMATION FOR SEQ ID NO:33:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:33:

Gln Glu Phe Asp Glu Met Glu Glu Cys Ala
1               5                   10

(2) INFORMATION FOR SEQ ID NO:34:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:34:

Ser His Leu Pro Tyr Ile Glu Gln Gly Met
1               5                   10

(2) INFORMATION FOR SEQ ID NO:35:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:35:

Met Glu Glu Cys Ala Ser His Leu Pro Tyr
1               5                   10

(2) INFORMATION FOR SEQ ID NO:36:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:36:

Asp Glu Met Glu Glu Cys Ala Ser His Leu Pro Tyr Ile Glu
1               5                   10

(2) INFORMATION FOR SEQ ID NO:37:

(i) SEQUENCE CHARACTERISTICS:
        (A) LENGTH: 12 amino acids
        (B) TYPE: amino acid
        (C) STRANDEDNESS: single (D) TOPOLOGY: linear (xi) SEQUENCE DESCRIPTION: SEQ ID NO:37:

```
Glu  Met  Glu  Glu  Cys  Ala  Ser  His  Leu  Pro  Tyr  Ile
1              5                        10
```

(2) INFORMATION FOR SEQ ID NO:38:

(i) SEQUENCE CHARACTERISTICS:
    (A) LENGTH: 10 amino acids
    (B) TYPE: amino acid
    (C) STRANDEDNESS: single
    (D) TOPOLOGY: linear (xi) SEQUENCE DESCRIPTION: SEQ ID NO:38:

```
Glu  Ala  Phe  Asp  Glu  Met  Glu  Glu  Cys  Ala
1              5                        10
```

(2) INFORMATION FOR SEQ ID NO:39:

(i) SEQUENCE CHARACTERISTICS:
    (A) LENGTH: 10 amino acids
    (B) TYPE: amino acid
    (C) STRANDEDNESS: single
    (D) TOPOLOGY: linear (xi) SEQUENCE DESCRIPTION: SEQ ID NO:39:

```
Ser  Arg  Ala  Ala  Leu  Ile  Glu  Glu  Gly  Gln
1              5                        10
```

(2) INFORMATION FOR SEQ ID NO:40:

(i) SEQUENCE CHARACTERISTICS:
    (A) LENGTH: 10 amino acids
    (B) TYPE: amino acid
    (C) STRANDEDNESS: single
    (D) TOPOLOGY: linear (xi) SEQUENCE DESCRIPTION: SEQ ID NO:40:

```
Met  Glu  Glu  Cys  Ala  Ser  Arg  Ala  Ala  Leu
1              5                        10
```

(2) INFORMATION FOR SEQ ID NO:41:

(i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:41:

```
Asp  Glu  Met  Glu  Glu  Cys  Ala  Ser  Arg  Ala  Ala  Leu  Ile  Glu
1              5                        10
```

(2) INFORMATION FOR SEQ ID NO:42:

(i) SEQUENCE CHARACTERISTICS:
    (A) LENGTH: 12 amino acids
    (B) TYPE: amino acid
    (C) STRANDEDNESS: single
    (D) TOPOLOGY: linear (xi) SEQUENCE DESCRIPTION: SEQ ID NO:42:

```
Glu  Met  Glu  Glu  Cys  Ala  Ser  Arg  Ala  Leu  Leu  Ile
1              5                        10
```